US012745908B2

(12) United States Patent
Gettys et al.

(10) Patent No.: US 12,745,908 B2
(45) **Date of Patent: *Sep. 29, 2026**

(54) SYSTEMS AND METHODS UTILIZING RAMAN SPECTROSCOPY FOR IN VIVO ANALYSIS

(71) Applicant: Boston Scientific Scimed, Inc., Maple Grove, MA (US)

(72) Inventors: Rebecca Jane Gettys, Carlisle, MA (US); Kirsten Viering, Newton, MA (US); George Wilfred Duval, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 4 days.

This patent is subject to a terminal disclaimer.

(21) Appl. No.: 18/971,211

(22) Filed: Dec. 6, 2024

(65) Prior Publication Data

US 2025/0090026 A1 Mar. 20, 2025

Related U.S. Application Data

(63) Continuation of application No. 17/858,141, filed on Jul. 6, 2022, now Pat. No. 12,186,056.

(Continued)

(51) Int. Cl.
*A61B 5/00* (2006.01)
*A61B 1/00* (2006.01)

(Continued)

(52) U.S. Cl.
CPC ........ *A61B 5/0075* (2013.01); *A61B 1/00045* (2013.01); *A61B 1/063* (2013.01); *A61B 1/07* (2013.01)

(58) Field of Classification Search
CPC ... A61B 5/0075; A61B 1/00045; A61B 1/063; A61B 1/07; A61B 5/0035; A61B 5/0084; A61B 5/7264
See application file for complete search history.

(56) References Cited

U.S. PATENT DOCUMENTS

| | | | |
|---|---|---|---|
| 9,877,655 | B2 | 1/2018 | Huang et al. |
| 10,105,041 | B2 | 10/2018 | Yamamoto et al. |

(Continued)

FOREIGN PATENT DOCUMENTS

| | | |
|---|---|---|
| WO | 2008154460 | 12/2008 |
| WO | 2022076879 | 4/2022 |

OTHER PUBLICATIONS

Daoust Francois et al.: "Handheld macroscopic Raman spectroscopy imaging instrument for machine-learning-based molecular tissue margins characterization", Journal of Biomedical Optics, SPIE, 1000 20th St. Bellingham WA 98225-6705 USA, vol. 26, No. 2, Feb. 1, 2021 (Feb. 1, 2021), p. 22911, XP060138747, ISSN: 1083-3668, DOI: 10.1117/1.JBQ.26.2.022911 (18 pages).

(Continued)

*Primary Examiner* — Alexei Bykhovski
(74) *Attorney, Agent, or Firm* — Bookoff McAndrews, PLLC

(57) ABSTRACT

A system for determining characteristics of tissue within a body of a patient may include a medical device. The medical device may include a distal end configured to be advanced within the body of the patient; at least one aperture at the distal end; a laser emitter operable to emit monochromatic light out from the distal end via the at least one aperture and onto target tissue; and at least one photodetector array. The at least one photodetector array may be configured to: receive light incident on the at least one aperture that is one or more of scattered by or reflected from the target tissue; and generate Raman spectroscopy image data based on (Continued)

monochromatic light incident on the at least one aperture, the Raman spectroscopy image data including an array of intensity values.

20 Claims, 9 Drawing Sheets

Related U.S. Application Data

(60) Provisional application No. 63/203,204, filed on Jul. 13, 2021.

(51) Int. Cl.
*A61B 1/06* (2006.01)
*A61B 1/07* (2006.01)

(56) References Cited

U.S. PATENT DOCUMENTS

| | | | | |
|---|---|---|---|---|
| 10,288,568 | B2 | 5/2019 | Zavaleta | |
| 10,401,883 | B2 | 9/2019 | Swanson et al. | |
| 2002/0156380 | A1* | 10/2002 | Feld | A61B 5/0086 250/341.8 |
| 2004/0064022 | A1 | 4/2004 | Korn | |
| 2006/0149134 | A1* | 7/2006 | Soper | A61B 5/066 600/109 |
| 2006/0155195 | A1 | 7/2006 | Maier et al. | |
| 2014/0316255 | A1 | 10/2014 | Garai et al. | |
| 2016/0358969 | A1 | 12/2016 | Fu et al. | |
| 2020/0323480 | A1* | 10/2020 | Shaked | A61B 3/0025 |

OTHER PUBLICATIONS

International Search Report and Written Opinion issued in International Application No. PCT/US2022/036169, issued Oct. 17, 2022 (15 pages).

Wikipedia, "Raman spectroscopy", https://en.wikipedia.org/wiki/Raman_spectroscopy, accessed Jan. 25, 2021 (25 pages).

Jermyn et al.: "Intraoperative brain cancer detection with Raman spectroscopy in humans", Science translational medicine 7.274 (2015): 274ra19-274ra19 (11 pages).

Ramirez-Elias et al.: "Raman spectroscopy for in vivo medical diagnosis", Raman Spectroscopy, Apr. 2018 (21 pages).

Kumamoto Yasuaki et al: "Rapid and accurate peripheral nerve imaging by multipoint Raman spectroscopy", Scientific Reports, vol. 7, No. 1, Apr. 12, 2017 (Apr. 12, 2017), XP093258121, US ISSN: 2045-2322, DOI: 10.1038/s41598-017-00995-y, Retrieved from the Internet: URL: https://www.nature.com/articles/s41598-017-00995-y.

* cited by examiner

SYSTEMS AND METHODS UTILIZING RAMAN SPECTROSCOPY FOR IN VIVO ANALYSIS

CROSS-REFERENCE TO RELATED APPLICATIONS

This application is a continuation of U.S. application Ser. No. 17/858,141, filed Jul. 6, 2022, which claims the benefit of priority of U.S. Provisional Patent Application No. 63/203,204, filed Jul. 13, 2021, the entirety of which is incorporated herein by reference.

TECHNICAL FIELD

Various embodiments of this disclosure relate generally to systems and methods for non-invasively determining characteristics of tissue within the body of a patient, and more particularly to machine-learning-based techniques for evaluating Raman spectroscopy images.

BACKGROUND

Delay of diagnosis and invasiveness of procedures are significant challenges in medical investigation and intervention. Many diagnoses require not only a tissue biopsy sample, which is generally invasive and may be traumatic on the body of a patient, but also ex vivo analysis of the sample, which generally adds a significant time delay and logistical complexity. For example, to make a diagnosis of colon cancer for a patient, endoscopy techniques are typically used to navigate to a target area of the patient's anatomy and take a biopsy sample which is then laboratory analyzed. Not only can this procedure be traumatic for the patient, but also the time between performing an endoscopy procedure and receiving results may be nontrivial. This problem may be compounded by the fact that only a small select portion of tissue is generally biopsied. If the accuracy of the biopsy was off, or if a portion of diseased tissue was not identified for biopsy, then this type of conventional procedure may miss or delay detection of disease, in addition to subjecting the patient to traumatic intervention.

Non-invasive tissue characterization techniques have been developed. Visual inspection is generally used, e.g., via a scope device. However, visual inspection is generally limited to a screening measure to identify potential sites for biopsy, and biopsy and laboratory analysis of a visually identified site is customarily required to determine a pathology. However, diseased tissue may not always be visually detectable, and thus visual inspection alone may miss the presence of disease.

This disclosure is directed to addressing above-referenced challenges. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the disclosure, methods and systems are disclosed for characterizing tissue within the body of a patient based on Raman spectroscopy images. In some embodiments, one or more machine-learning techniques are used to analyze Raman spectroscopy images.

In one aspect, an exemplary system for determining characteristics of tissue within a body of a patient, may include a medical device. The medical device may include a distal end configured to be advanced within the body of the patient; at least one aperture at the distal end; a laser emitter operable to emit monochromatic light out from the distal end via the at least one aperture and onto target tissue; and at least one photodetector array configured to: receive light incident on the at least one aperture that is one or more of scattered by or reflected from the target tissue; and generate Raman spectroscopy image data based on monochromatic light incident on the at least one aperture, the Raman spectroscopy image data including an array of intensity values.

In some embodiments, the system may further include: a display; and an image processing device that is operatively connected to the display, that is configured to receive the Raman spectroscopy image data from the medical device. The image processing device may include a memory storing instructions; and at least one processor operatively connected to the memory and configured to execute the instructions to perform operations. The operations may include: applying learned associations between one or more training tissue characteristics and training Raman spectroscopy image data to the Raman spectroscopy image data received from the medical device to determine one or more tissue characteristics of the target tissue; and causing the display to output information associated with the one or more tissue characteristics of the target tissue.

In some embodiments, applying the learned associations to the Raman spectroscopy image data received from the medical device includes inputting the Raman spectroscopy image data into a trained machine-learning model. In some embodiments, the trained machine-learning model developed the learned associations based on the one or more training tissue characteristics as ground truth and the training Raman spectroscopy image data as training data. In some embodiments, the trained machine-learning model is configured to use the learned associations to output the one or more tissue characteristics of the target tissue in response to the input of the Raman spectroscopy image data.

In some embodiments, the medical device further includes a location sensor positioned at the distal end and configured to generate a position signal. The operations may further include: receiving a three-dimensional model of at least portion of an interior of the body of the patient; and receiving the position signal from the medical device, and registering a position of the distal end of the medical device with a location within the three-dimensional model. In some embodiments, one or more of: the determination of the one or more tissue characteristics of the target tissue is further based on the location of the distal end within the three-dimensional model; or the operations further include outputting a visual indication of the location of the distal end within the three-dimensional model.

In some embodiments, the medical device further includes a visible light emitter operable to emit visible light out from the distal end via the at least one aperture; and the at least one photodetector array is further configured to generate visible image data based on visible light incident on the at least one aperture.

In some embodiments, the image processing device is further configured to receive the visible image data from the medical device; and the operations further include causing the display to output a live video feed of an interior of the body of the patient based on the visible image data received from the medical device.

In some embodiments, the operations further include: registering, based on the Raman spectroscopy image data, one or more regions of the visible image data; that correspond with the one or more tissue characteristics of the target tissue; and generating one or more visual indicators associated with the one or more tissue characteristics of the target tissue. In some embodiments, one or more of: the determination of the one or more tissue characteristics of the target tissue is further based on the visible image data and a registration of the visible image data with the Raman spectroscopy image data; or the operations further include causing the display to overlay the one or more visual indicators on the live video feed at the one or more corresponding regions.

In some embodiments, the system may further include a controller configured to alternatingly operate the laser emitter and the visible light emitter such that operation of the laser emitter is interlaced between frames of the live video feed.

In some embodiments, the medical device further includes: a proximal handle portion; and at least one fiber optic line. In some embodiments, the laser emitter and the visible light emitter are positioned in the proximal handle portion, and are operatively connected to the at least one aperture via the at least one fiber optic line.

In some embodiments, the at least one fiber optic line includes only a single fiber optic line that has an operative connection selectable between the laser emitter and the visible light emitter.

In some embodiments, the at least one photodetector array is a single RGB-IR photodetector array.

In some embodiments, the laser emitter has a selectable frequency, different selectable frequencies corresponding to different tissue characteristics.

In some embodiments, the medical device further includes: a proximal handle portion; and at least one fiber optic line. In some embodiments, the at least one photodetector array is positioned in the proximal handle portion, and is operatively connected to the at least one aperture via the at least one fiber optic line.

In some embodiments, the medical device further includes: a modulation device configured to apply an intermodulation frequency to the monochromatic light emitted by the laser emitter; and a demodulation device configured to apply a demodulation frequency to the Raman spectroscopy image data based on the intermodulation frequency.

In some embodiments, the medical device further includes one or more light filters applied to the at least one aperture. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION OF EMBODIMENTS

Figure 1:
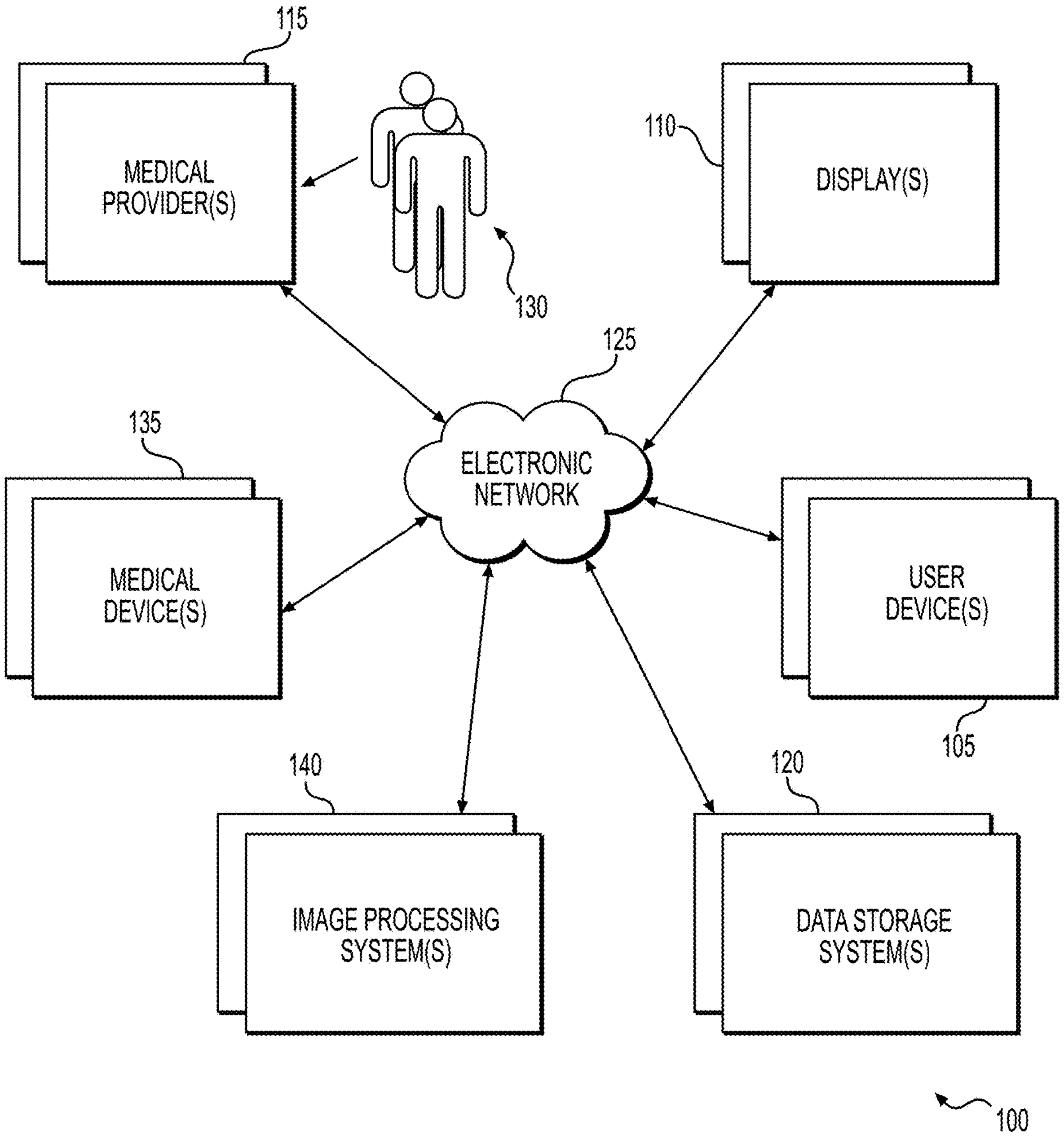
FIG. 1 depicts an exemplary system for determining one or more characteristics of tissue within the body of a patient, according to one or more embodiments.

According to certain aspects of the disclosure, methods and systems are disclosed for non-invasive techniques for characterizing tissue within the body of a patient, e.g., via Raman spectroscopy image analysis. It is generally desirably to reduce procedure time, decrease invasiveness of procedures, and reduce delay between performing a diagnostic procedure and determining a diagnosis. However, conventional techniques may not be suitable. For example, conventional techniques may not be able to characterize relatively large regions of tissue within the patient's body without significantly adding to procedure time. Conventional techniques may also rely on accurate pre-procedure identification of tissue portions for investigation and on accurate targeting of identified tissue portions during the procedure, which may compound the risk of error or inaccurate diagnosis. Accordingly, improvements in technology relating to non-invasive tissue characterization techniques are needed.

As will be discussed in more detail below, in various embodiments, systems and methods are described for tissue characterization, and in particular non-invasive tissue characterization, via analysis of Raman spectroscopy image data. In some embodiments, machine-learning is used. By using learned associations between Raman spectroscopy image data and tissue characteristic data, and/or other factors, target tissue within the body of a patient may be characterized, e.g., non-invasively.

Reference to any particular activity or procedure is provided in this disclosure only for convenience and not intended to limit the disclosure. A person of ordinary skill in the art would recognize that the concepts underlying the disclosed devices and methods may be utilized in any suitable activity. The disclosure may be understood with reference to the following description and the appended drawings, wherein like elements are referred to with the same reference numerals.

The terminology used below may be interpreted in its broadest reasonable manner, even though it is being used in conjunction with a detailed description of certain specific examples of this disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

For ease of description, portions of the device and/or its components are referred to as proximal and distal portions. It should be noted that the term "proximal" is intended to refer to portions closer to a user of the device, and the term "distal" is used herein to refer to portions further away from the user. Similarly, extends "distally" indicates that a component extends in a distal direction, and extends "proximally" indicates that a component extends in a proximal direction.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. The term "or" is used disjunctively, such that "at least one of A or B" includes, (A), (B), (A and A), (A and B), etc. Relative terms, such as, "substantially" and "generally," are used to indicate a possible variation of ±10% of a stated or understood value.

As used herein, terms such as "image data" or the like generally encompass one or more of signals, values, data, or the like that are representative of, usable to generate, or descriptive of an image. Image data may include, for example, an array of values corresponding to pixels, voxels, or the like that collectively form an image, a signal representative of such values, or the like. The values may be indicative of intensity, e.g., brightness or color in a visible image, may be indicative of a frequency response, e.g., in a spectroscopy image, or the like. An image may have two dimensions, three dimensions, or any suitable number of dimensions. Image data may be transmitted as a signal, e.g., a data transmission from an image sensor such as a photodetector array and/or between one or more devices, and may be stored as a data file, e.g., an array or matrix, or any other suitable file type.

As used herein, terms such as "medical imaging data" or the like generally encompass data associated with and/or indicative of a geometry and/or physiology of a patient, e.g., that may be generated via medical imaging and/or that may be represented as an image of the anatomy of the patient, e.g., a two-dimensional image, a three-dimensional image or model, a video, a time-varying image, etc. Medical imaging generally encompasses techniques whereby a signal (light, electromagnetic energy, radiation, etc.) is generated, and measurements are taken that are indicative of how that signal interacts with and/or is affected by, transmitted through, or the like, the patient. Examples of medical imaging technologies include CT scans, MRI scans, X-rays, or any other suitable modality, e.g., that may be used to visualize an interior of at least a portion of the patient's anatomy. Medical imaging data may include, for example, two-dimensional data and/or images, three-dimensional data and/or images, voxel data, a geometric model of at least a portion of patient anatomy, a solid model of the portion of patient anatomy, a mesh of nodes or points representative of the portion of the anatomy and/or characteristics of the portion of the anatomy, and/or any other suitable data associated with the patient and/or medical imaging.

As used herein, terms such as "tissue" generally encompass biological material of a patient. However, it should be understood that, in some embodiments, techniques disclosed herein may be applicable and/or applied to other material, e.g., biological byproducts such as substances left behind by bacteria, foreign substances within the body of the patient, or the like. Thus, where the term "tissue" is used, it should be understood that similar techniques are also contemplated that pertain to such other materials.

As used herein, the term tissue "characteristic" generally encompasses a quantifiable or qualitative trait of the tissue. For example, characteristics of tissue may include, for example, one or more of a type of tissue (e.g., connective tissue, epithelial tissue, muscle tissue, nervous tissue, or tissue associated with a particular organ such as pancreatic tissue, liver tissue, colonic tissue, etc.), a health condition of the tissue, a presence of disease (e.g., a presence of cancer and/or a particular type of cancer), a severity of a present disease (e.g., a stage of a present cancer), a presence and/or amount of inflammation, a presence of bacteria or other foreign material, or the like.

As used herein the term "medical provider" generally encompasses a person, e.g., a doctor, clinician, nurse, medical professional, etc., using a computer system and/or medical device, the computer system and/or medical device itself, an entity that is associated with, e.g., owns or operates, the computer system and/or medical device, or an agent or intermediary thereof. For example, a medical provider may include a person or persons performing a procedure, a medical imaging device such as a CT scanner, an entity such as a hospital or outpatient facility that uses a medical imaging device, a medical data exchange system, or the like. A medical provider may, for example, perform a procedure on a patient, generate or otherwise obtain patient data such as medical imaging data and/or diagnostic data, e.g., by performing medical imaging and/or a diagnostic procedure on a patient or tissue therefrom, and/or perform analysis of the obtained patient data.

As used herein, a "machine-learning model" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine-learning model is generally trained using training data, e.g., experiential data and/or samples of input data, which are fed into the model in order to establish, tune, or modify one or more aspects of the model, e.g., the weights, biases, criteria for forming classifications or clusters, or the like. Aspects of a machine-learning model may operate on an input linearly, in parallel, via a network (e.g., a neural network), or via any suitable configuration.

The execution of the machine-learning model may include deployment of one or more machine learning techniques, such as linear regression, logistical regression, random forest, gradient boosted machine (GBM), deep learning, and/or a deep neural network. Any suitable training technique may be employed. For example, supervised learning may include providing training data and labels corresponding to the training data, e.g., as ground truth. Examples of training techniques include stochastic training, gradient boosted training, random seeded training, recursive training, epoch or batch-based training, etc.

A medical provider may desire to determine a diagnosis of a patient. For example, the medical provider may desire to determine whether the patient has or is at risk of developing a disease or illness such as infection or cancer. In a particular example, a medical provider may desire to diagnose a presence or risk of colorectal cancer exemplified by cancerous tissue in the tissue lining of the large intestine or colon. Conventionally, visual inspection, e.g., via an endoscope such as a colonoscope or the like, is used by the medical provider to disambiguate between healthy and/or scarred tissue and a lesion or other tissue that may be cancerous, whereby a biopsy of suspect tissue is taken for laboratory analysis. However, as mentioned above, such conventional techniques may be inaccurate, traumatic for the patient, and may include a time delay before a diagnosis is determined. Thus, a medical provider may desire to use a system for characterizing tissue that improves accuracy and/or efficiency at identifying suspect tissue, reduces and/or eliminates the need for biopsies, and/or reduces or eliminates the time delay caused by laboratory analysis.

In an exemplary use case, a medical provider may advance a distal end of a medical device, e.g., an endoscope, into a body of a patient. A white light emitter of the medical device may be operated to emit white light out from an aperture of the distal end of the medical device so as to illuminate an interior of the body. A visual channel, such as a camera, fiber optic channel, or the like, on the distal end of the medical device may be used to generate visual imaging of the interior of the body, e.g., for navigational purposes within the body of the patient. A laser emitter of the medical device may be operated to emit monochromatic light out from an aperture of the distal end of the medical device and onto tissue within the body. While a portion of the monochromatic light may be absorbed by or transmitted through the tissue, at least some of the monochromatic light may be scattered and/or reflected by the tissue. Most of the scattered light may have a same frequency as the monochromatic light emitted by the laser emitter. However, some of the scattered light may either lose energy or gain energy due to an interaction between the scattered light and vibrational energy state(s) of molecules in the tissue, and thereby experience a frequency shift downwards or upwards, respectively. As the vibrational energy states are molecule specific, the frequency shift in the scattered light is usable to identify a molecular structure of the tissue via Raman spectroscopy techniques, whereby a sensor is used to characterize the scattered light.

While endoscope devices have been used for tissue characterization, such devices may include one or more of the risks or deficiencies in conventional techniques discussed above. Thus, the medical device employed by the medical provider may include at least one photodetector array configured to receive the scattered light from the tissue. The at least one photodetector may be configured to generate Raman spectroscopy image data based on the received light. The value recorded by each pixel of the at least one photodetector array may be indicative of a frequency response of that pixel to the received scattered light. An image processing device operatively connected to the medical device may receive the Raman spectroscopy image data, and determine one or more characteristics of the tissue therefrom.

Raman spectroscopy image data, e.g., based on an array of frequency responses from the pixels, may be used to provide a location-based characterization of tissue. In other words, Raman spectroscopy image data may be used to locate where in the tissue, within a field of view of the at least one photodetector array, potentially diseased tissue and/or foreign material may be located, as well as feature or shape information that may not be discernable with the conventional sensor.

As noted above, in some cases, the medical device may include a visual channel, e.g., a visible light emitter and a visible light sensor or optical viewer usable by the medical provider to view the interior of the body of the patient, e.g., via a scope, a lens, or an output device connected to the medical device such as a monitor. The Raman spectroscopy image data may be used to generate a visual indicator representative of one or more characteristics of the tissue, and the visual indicator may be overlaid on the endoscopic view so that the location of the tissue exhibiting the determined characteristics is identified in the endoscopic view.

In an illustrative example, both the view via the visual channel and the characterization of the tissue via the Raman spectroscopy image data may occur in real time or near real time. As a result, the medical provider may be able to view characterizations of tissue during, for example, the ordinary course of the endoscopic procedure.

In some instances, the characterization of tissue may be used to identify locations within the body of the patient to be biopsied. In other words, the characterization of tissue may be used as a screening tool that may one or more of improve the accuracy of location selection for biopsy, decrease the amount of biopsies needed, detect locations for biopsies that may not have been evident to the visual inspection of the medical provider, decrease an amount of time for the procedure, or decrease time to diagnosis. In some instances, the characterization may replace and/or obviate the need for a biopsy.

In another illustrative use case, the image processing device may use one or more machine-learning techniques to characterize the tissue based on the Raman spectroscopy image data. For example, one or more machine-learning techniques may be used to develop or learn associations between tissue characteristics and Raman spectroscopy image data. Other data may also be used in conjunction with the Raman spectroscopy image data such as, for example, medical imaging data, patient data, the visual channel of the medical device, or the like.

It should be understood that the examples above are illustrative only. While some of the examples above include machine-learning techniques, e.g., for image analysis and/or characterization of tissue, it should be understood that any suitable technique for such tasks may be used. Further, the techniques and technologies of this disclosure may be adapted to any suitable activity.

Presented below are various aspects of Raman spectroscopy image analysis techniques that may be adapted to characterizing tissue within the body of a patient. As will be discussed in more detail below, in some embodiments, machine learning techniques associated with Raman spectroscopy image analysis may include one or more aspects according to this disclosure, e.g., a particular selection of training data, a particular training process for a machine-learning model, operation of a particular device suitable for use with the trained machine-learning model, operation of the machine-learning model in conjunction with particular data, modification of such particular data by the machine-learning model, etc., and/or other aspects that may be apparent to one of ordinary skill in the art based on this disclosure.

FIG. 1 depicts an exemplary system 100 that may be utilized with techniques presented herein. One or more user device(s) 105, one or more display(s) 110, one or more medical provider(s) 115, and one or more data storage system(s) 120 may communicate across an electronic network 125. The medical provider 115 may be associated with a medical procedure, a medical imaging, a diagnosis, or the like, for one or more patient(s) 130. As will be discussed in further detail below, one or more medical device(s) 135 and one or more image processing device(s) 140 may communicate with each other and/or one or more of the other components of the system 100 across electronic network 125.

In some embodiments, the components of the system 100 are associated with a common entity, e.g., a hospital, surgery center outpatient imaging center, or the like. In some embodiments, one or more of the components of the system 100 is associated with a different entity than another. The components and devices of the system 100 may communicate in any arrangement. As will be discussed herein, systems and/or devices of the system 100 may communicate in order to characterize tissue of a patient.

The user device 105 may be configured to enable access and/or interaction with other systems and/or devices in the system 100, e.g., by the medical provider 115 or another user. For example, the user device 105 may be a computer system such as, for example, a desktop computer, a mobile device, a tablet, etc. In some embodiments, the user device 105 may include one or more electronic application(s), e.g., a program, plugin, browser extension, etc., installed on a memory of the user device 105. In some embodiments, the electronic application(s) may be associated with one or more of the other components in the system 100. For example, the electronic application(s) may include one or more of system control software, system monitoring software, software development tools, etc. In some embodiments, the user device 105 may be usable to one or more of operate, control, or monitor other components of the system 100 and/or generate, store, or transmit data associated with such actions.

The display 110 may include a monitor, screen, or the like configured to output images and information. In some embodiments, the display 110 may include or be associated with an input device, e.g., a touch screen, tablet, or the like. In some embodiments, the medical provider 115 may include a system or device configured to act as an input device for the display 110, e.g., the user device 105.

The data storage system 120 may include a server system, an electronic medical data system, computer-readable memory such as a hard drive, flash drive, disk, etc. In some embodiments, the data storage system 120 may include and/or interact with an application programming interface for exchanging data to other systems, e.g., one or more of the other components of the system 100. The data storage system 120 may include and/or act as a repository or source for patient data, medical imaging data, Raman spectroscopy image data, training data for a machine-learning model, or the like.

In various embodiments, the electronic network 125 may be a wide area network ("WAN"), a local area network ("LAN"), personal area network ("PAN"), a wired or wireless connection between devices, or the like. In some embodiments, electronic network 125 includes the Internet, and information and data provided between various systems occurs online. "Online" may mean connecting to or accessing source data or information from a location remote from other devices or networks coupled to the Internet. Alternatively, "online" may refer to connecting or accessing an electronic network (wired or wireless) via a mobile communications network or device. The Internet is a worldwide system of computer networks-a network of networks in which a party at one computer or other device connected to the network can obtain information from any other computer and communicate with parties of other computers or devices. The most widely used part of the Internet is the World Wide Web (often-abbreviated "WWW" or called "the Web"). A "website page" generally encompasses a location, data store, or the like that is, for example, hosted and/or operated by a computer system so as to be accessible online, and that may include data configured to cause a program such as a web browser to perform operations such as send, receive, or process data, generate a visual display and/or an interactive interface, or the like.

Further aspects of the medical device 135 are discussed in more detail below with regard to FIGS. 2 and 3. The image processing device 140 may be configured to characterize the target tissue of the patient 130 based on data received from the medical device 135, e.g., Raman spectroscopy image data associated with target tissue within the patient 130.

Raman spectroscopy image data may include, for example, an array of values indicative of a frequency response at different pixels of a photodetector array. Further aspects of the photodetector array and how Raman spectroscopy data may be generated are discussed in further detail below. Compared to spectrum data from a Raman spectroscopy sensor, which provides a frequency response of the sensor as a whole, the array of frequency response values may provide not only frequency response, but also shape and/or feature information associated with the frequency response.

In some embodiments, the image processing device 140 may be configured to compare the Raman spectroscopy image data with a predetermined criteria to determine one or more characteristics of the target tissue. For example, detection of a threshold amount (e.g., by a threshold number of pixels) of a particular frequency may be indicative of a particular characteristic for target tissue. In another example, a particular shape or arrangement of pixels or values exhibiting a particular frequency may be indicative of a particular characteristic for target tissue. In some embodiments, one or more aspects of the Raman spectroscopy image data is compared with Raman spectroscopy image data of tissue with known characteristics to determine one or more similarity scores, and one or more characteristics of the target tissue may be determined based on the similarity scores.

In some embodiments, the image processing device 140 may apply a decision tree algorithm or the like that is based on the predetermined criteria. In some embodiments, the image processing device 140 may compute metrics that quantitatively assess how well each criterion is satisfied, and may determine one or more characteristics based on the metrics. Any suitable image analysis and/or tissue characterization technique may be used.

In some embodiments, the image processing device 140 may apply one or more machine-learning techniques to one or more of analyze data or determine tissue characteristics based on the analyzed data. In some embodiments, the image processing device 140 may one or more of (i) generate, store, train, or use a machine-learning model configured to analyze image data and/or characterize tissue. The image processing device 140 may include a machine-learning model and/or instructions associated with the machine-learning model, e.g., instructions for generating a machine-learning model, training the machine-learning model, using the machine-learning model etc. The image processing device 140 may include instructions for retrieving Raman spectroscopy data, medical imaging data, patient data, or the like, adjusting such data, e.g., based on the output of the machine-learning model, and/or operating the display 110 to output information associated with characterizations of tissue, e.g., as adjusted based on the machine-learning model. The image processing device 140 may include training data, e.g., Raman spectroscopy image data, visible image data, medical imaging data or the like associated with training tissue, and may include ground truth data, e.g., characterizations of the training tissue.

In some embodiments, a system or device other than the image processing device 140 is used to generate and/or train the machine-learning model. For example, the user device 105 may include instructions for generating the machine-learning model, the training data and ground truth, and/or instructions for training the machine-learning model. A resulting trained-machine-learning model may then be provided to the image processing device 140. Although depicted together in the system 100 in FIG. 1, it should be understood that, in some embodiments, after the trained-machine-learning model is provided to the image processing device 140, the system used to generate and/or train the machine-learning model may not maintain connection with one or more of the components of the system 100.

Generally, a machine-learning model includes a set of variables, e.g., nodes, neurons, filters, etc., that are tuned, e.g., weighted or biased, to different values via the application of training data. In supervised learning, e.g., where a ground truth is known for the training data provided, training may proceed by feeding a sample of training data into a model with variables set at initialized values, e.g., at random, based on Gaussian noise, a pre-trained model, or the like. The output may be compared with the ground truth to determine an error, which may then be back-propagated through the model to adjust the values of the variable.

Training may be conducted in any suitable manner, e.g., in batches, and may include any suitable training methodology, e.g., stochastic or non-stochastic gradient descent, gradient boosting, random forest, etc. In some embodiments, a portion of the training data may be withheld during training and/or used to validate the trained machine-learning model, e.g., compare the output of the trained model with the ground truth for that portion of the training data to evaluate an accuracy of the trained model. The training of the machine-learning model may be configured to cause the machine-learning model to one or more of learn or detect features or shapes in image data such as Raman spectroscopy image data, or learn associations between Raman spectroscopy image data, visible image data, medical imaging data, patient data, etc., associated with training target tissue and one or more tissue characteristics of the training target tissue, such that the trained machine-learning model is configured to determine an output of one or more tissue characteristics in response to input of Raman spectroscopy image data and optionally other data based on the learned associations.

In various embodiments, the variables of a machine-learning model may be interrelated in any suitable arrangement in order to generate the output. For example, in some embodiments, the machine-learning model may include image-processing architecture that is configured to identify, isolate, and/or extract features, geometry, and or structure in one or more of the medical imaging data and/or the non-optical in vivo image data. For example, the machine-learning model may include one or more convolutional neural network ("CNN") configured to identify features in the Raman spectroscopy image data and/or the visible image data, and may include further architecture, e.g., a connected layer, neural network, etc., configured to determine a relationship between the identified features in order to determine a tissue characteristic.

In some embodiments, the CNN may be pre-trained. For example, feature detection in image analysis may utilize learned relationships regarding features or shapes that may be present in a wide variety of mediums. A CNN may be pre-trained, e.g., on generic data or data unspecific to the particular machine-learning operation. Pre-training a CNN may reduce the time and/or number of samples needed to train the CNN on training data specific to the intended operation.

In some embodiments, a CNN may be trained that accepts multiple items as inputs. For example, a CNN may be trained to detect features based on input of a combination of Raman spectroscopy image data associated with training target tissue and visual image data associated with the training target tissue. Other data that may be used as an additional or alternative input for a CNN may include, for example, medical image data, patient data, demographic data, etc.

In some embodiments, training data that includes all of the types of data to be used as input for the CNN may be unavailable and/or costly or difficult to obtain. For example, while visual image data and tissue characteristics for various tissue samples may be readily available, Raman spectroscopy image data for such samples may not be as readily available. In some embodiments, a CNN may be pre-trained based on partial input data. For example, null data and/or a copy of another input such as the visual image data may be used in place of the Raman spectroscopy image data when pre-training the CNN. Such pre-training may reduce the number of Raman spectroscopy image data samples needed to train the CNN.

In some embodiments, the Raman spectroscopy image data may be mapped to anatomical geometric data. As noted above, Raman spectroscopy image data include an array of values, e.g., that may be represented as a two-dimensional image. Anatomical geometric data, which may be reconstructed from one or more of visible image data, medical imaging data, or the like, may include a three-dimensional representation of a portion of anatomy including the tissue that resulted in the Raman spectroscopy image data. The image processing device 140 may map the values of the Raman spectroscopy image data to three-dimensional positions in the anatomical geometric data in order to generate three-dimensional Raman spectroscopy image data. In an example, a depth value may be added to each value in the array. In a similar manner, tissue characterizations that are associated with particular regions of the tissue may be mapped onto the anatomical geometric data. Such three-dimensional data may be used as inputs to a CNN.

In some instances, different samples of training data and/or input data may not be independent. For example, image data may be acquired sequentially, e.g., as the medical device 135 is navigated through the body of the patient 130. Different views and/or view angles of a region of tissue may provide more information than that of a single view. Thus, in some embodiments, the machine-learning model may be configured to account for and/or determine relationships between multiple samples.

For example, in some embodiments, the machine-learning model of the image processing device 140 may include a Recurrent Neural Network ("RNN"). Generally, RNNs are a class of feed-forward neural networks that may be well adapted to processing a sequence of inputs. In some embodiments, the machine-learning model may include a Long Short Term Memory ("LSTM") model. An LSTM model may be configured to generate an output from a sample that takes at least some previous samples and/or outputs into account.

Although depicted as separate components in FIG. 1, it should be understood that a component or portion of a component in the system 100 may, in some embodiments, be integrated with or incorporated into one or more other components. For example, a portion of the display 110 may be integrated into the user device 105, or the like. At least a portion of the image processing device 140 may be integrated into the medical device 135 (e.g., in an onboard graphics-processing unit or a field-programmable-gate array, or the like), into the user device 105, a medical imaging device associated with the medical provider 115, the data storage system 120, or the like. In some embodiments, operations or aspects of one or more of the components discussed above may be distributed amongst one or more other components. Any suitable arrangement and/or integration of the various systems and devices of the system 100 may be used.

Figure 2A:
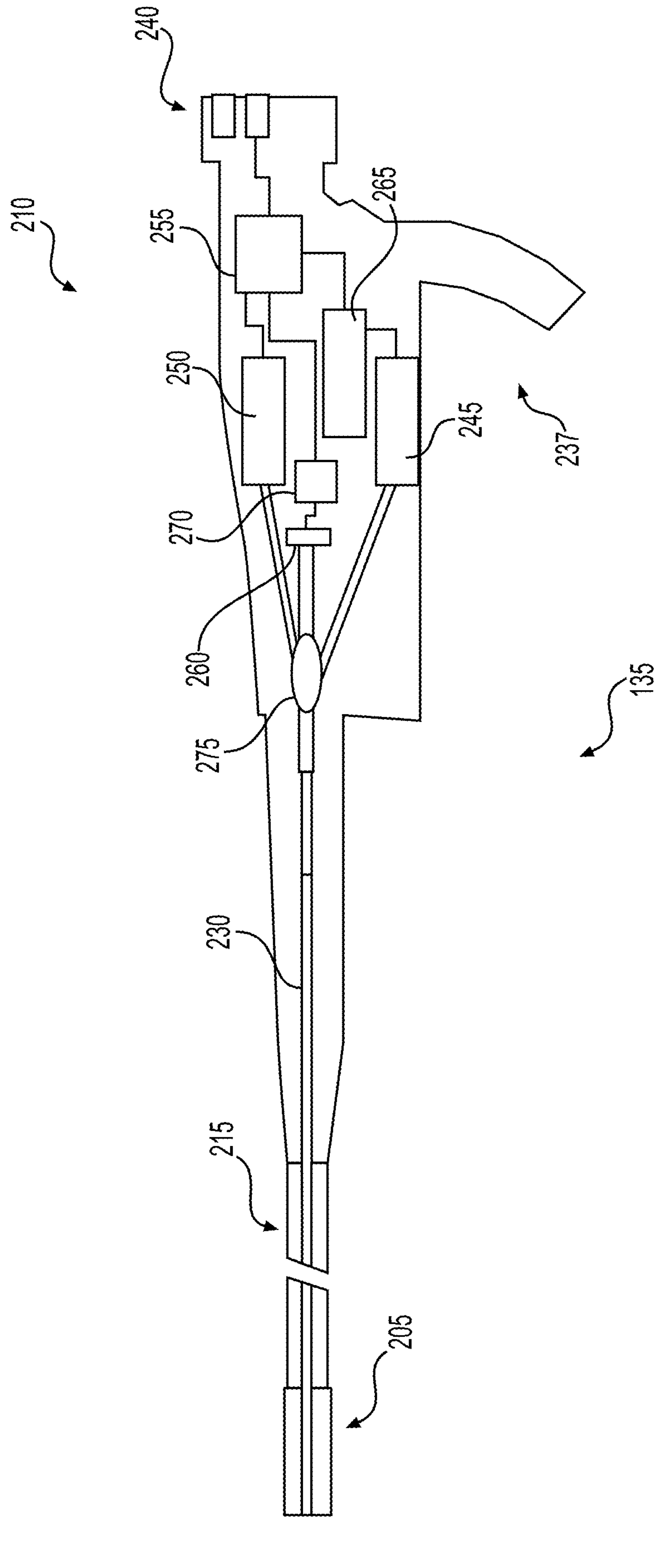
FIG. 2A depicts an exemplary embodiment of a medical device from the system of FIG. 1.

FIG. 2A depicts an exemplary embodiment 200 of the medical device 135. However, it should be understood that the embodiment in FIG. 2A is illustrative only, and that any suitable medical device for characterizing target tissue of the patient 130 may be used. The medical device 135 may be, for example, an endoscope (e.g., a colonoscope, bronchoscope, etc.) and may include a distal end 205 connected to a proximal end 210 via a tube 215.

In some embodiments, at least a portion of the medical device 135 is configured to be disposable, e.g., the distal end 205 and or the tube 215. In some embodiments, one or more of the proximal end 210, tube 215, and distal end 205 are separable from each other, e.g., so that a portion may be disposed of and replaced. In some embodiments, an entirety of the medical device 135 is configured to be disposable.

Figure 2B:
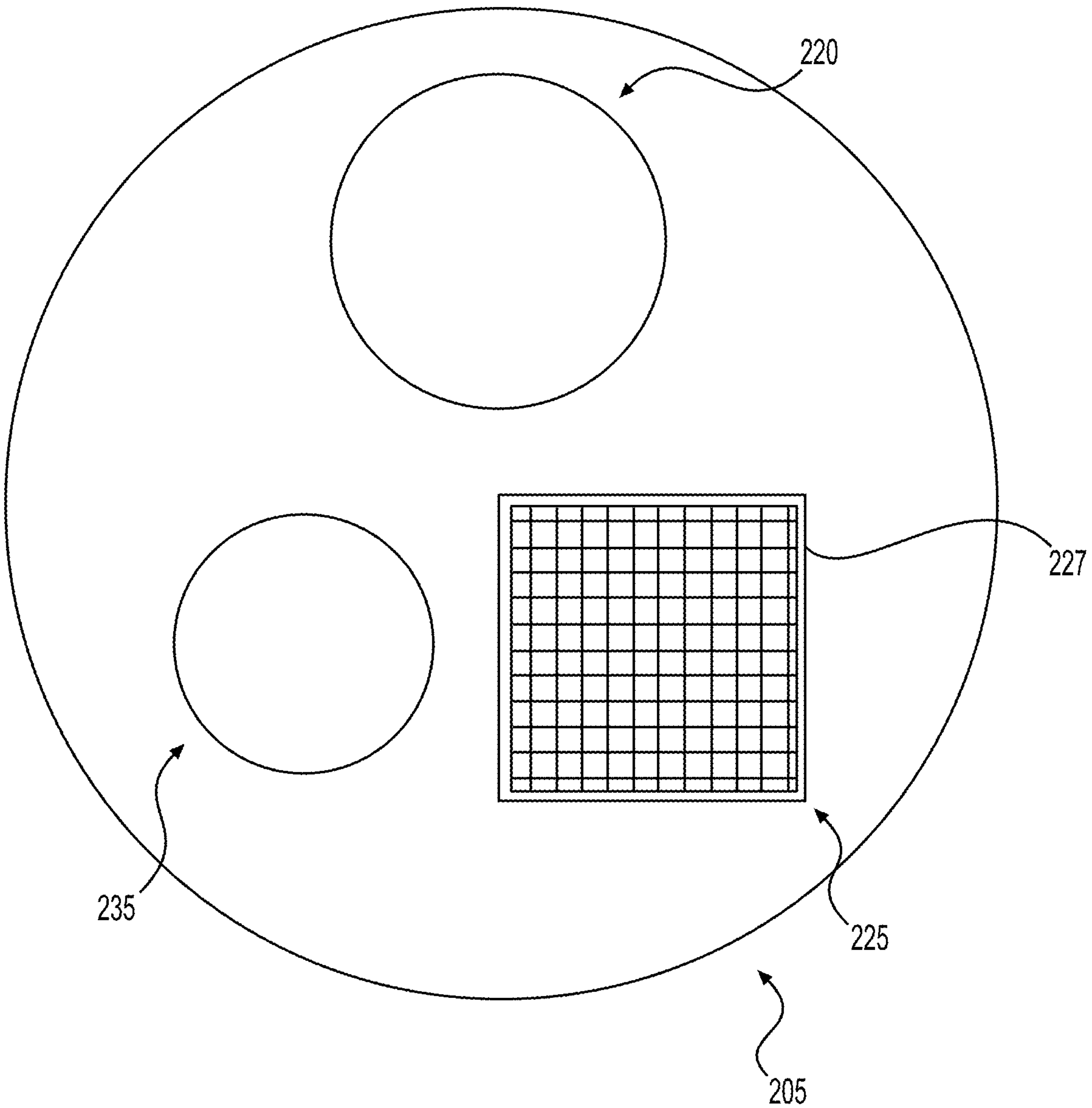
FIG. 2B depicts an end view of the distal end of the medical device of FIG. 2A.

FIG. 2B depicts an end view of the distal end 205 of FIG. 2A. The distal end 205 may include one or more opening(s) 220, at least one aperture 225, one or more optical elements 227, or a location sensor 235. The opening 220 may be configured to one or more of receive a component or communicate with a lumen, e.g., a working channel (not shown), disposed in the tube 215. Illustrative examples of such a component include a diagnostic or therapeutic tool, such as a grasper, forceps, knife, ablative catheter, etc. The opening 220 may include, for example, an orifice for taking in or outputting fluid and/or material, such as insufflating gas, irrigation fluid, etc. Further aspects of the aperture(s) 225 are discussed below.

The optical element(s) 227 may include, for example, one or more of a light filter, a lens, a prism, a polarizer, etc. The optical element(s) 227 may be positioned on or over at least a portion of the at least one aperture 225. Different light filter(s) of the optical element(s) 227 may be configured to filter different colors and/or wavelengths of light, such that different portions of the aperture(s) are configured to pass different colors and/or wavelengths of light there-through. In some embodiments, the optical elements 227 may be positioned in different locations, as discussed in further detail below.

The location sensor 235 may include, for example, an electromagnetic position sensor that uses one or more electromagnetic signals usable to determine a three-dimensional location of the distal end 205. However, in various embodiments, any suitable type of location sensor may be used.

Returning to FIG. 2A, the tube 215 may be formed from a flexible material. The tube 215 may include at least one fiber optic line 230 and one or more lumens (not shown) that communicate between the distal end 205 and the proximal end 210. In some embodiments, the tube 215 may further include and/or house other elements such as a wire connector configured to communicate data between a component at the distal end 205, and the proximal end 210.

The proximal end 210 may include, for example, a handle portion 237 and one or more interface(s) 240. The handle portion 237 may be configured to enable an operator to manipulate, advance, retract, and/or orient the distal end 205. The interface 240 may include, for example, a user control for operating the medical device 135, an umbilicus to output data, send or receive electrical signals, and/or communicate a fluid or material into or out from the medical device 135. An interface 240 for data may include one or more of a wired or wireless connection. The interface 240 may also be configured to receive power for operating a component disposed at the distal end 205.

The proximal end 210 may further include one or more of a laser emitter 245, a visible light emitter 250, a controller 255, at least one photodetector array 260, a modulation device 265, a demodulation device 270, or a selectable connector 275. In various embodiments, one or more of these components may be positioned in and/or at least partially integrated into a separate device, e.g., the image processing device 140 and/or a separate control box wired or wirelessly connected to the medical device 135.

The laser emitter 245 may be operable to emit monochromatic light. Any suitable frequency of monochromatic light may be used. For example, infra-red (IR) light or near-infrared (nIR) light, such as light having a wavlength of 785 nm or 1,064 nm, may be used. In some embodiments, different tissue characteristics may be associated with, e.g., may be detectable via, monochromatic light of different frequencies. In some embodiments, the laser emitter 245 is configured to emit monochromatic light at a selectable frequency, e.g., via control of current or voltage supplied to the laser emitter 245. The laser emitter 245 may be operatively connected to the at least one aperture 225, e.g., by the at least one fiber optic line 230, such that monochromatic light emitted by the laser emitter 245 is emitted out from the distal end 205 of the medical device 135 via the at least one aperture 225.

In some embodiments, such as the embodiment in FIG. 2A, the modulation device 265 may be operatively connected to the laser emitter 245. The modulation device 265 may be configured to apply an intermodulation frequency to the monochromatic light emitted by the laser emitter 245. In some embodiments, the modulation device 265 may, for example, apply the intermodulation frequency by adjusting the selectable frequency of the laser emitter 245, e.g., in a continuous cyclical manner. In some embodiments, the modulation device 265 may include a further laser emitter that is operated in conjunction with the laser emitter 245.

As noted in some of the examples above, when the medical device 135 is positioned within the body of the patient 130, the monochromatic light of the laser emitter 245 may be emitted out from the distal end 205 of the medical device 135 via the at least one aperture 225, and onto target tissue within the body of the patient 130. And, as also noted above, at least a portion of the monochromatic light may be scattered and/or reflected back toward the distal end 205 of the medical device 135. Moreover, the frequency of a portion of the scattered light may be shifted due to interaction with vibrational energy state(s) of molecules in the tissue.

The at least one photodetector array 260 may be configured to receive incident light, e.g., the light scattered and/or reflected by the target tissue. For example, in the embodiment depicted in FIG. 2A, the at least one photodetector array 260 may be operatively connected to the at least one aperture 225 via the at least one fiber optic line 230. In some embodiments, different fiber optic line(s) 230 are used to connect the emitter(s) to the aperture(s) than are used to connect the photodetector(s) to the aperture(s). The at least one photodetector array 260 may include an array of sensing regions, e.g., pixels, that are configured to generate Raman spectroscopy image data based on the received light. Any suitable type of photodetector array may be used, such as examples discussed in more detail below.

As noted above, Raman spectroscopy is associated with the frequency shift of scattered light resulting from interaction between the monochromatic light emitted by the laser emitter 245 and the target tissue. In some embodiments, the pixels are configured to detect variation in the frequency of the monochromatic light received by the at least one photodetector array 260. In some embodiments, one or more of the optical element(s) 227, e.g., one or more filter(s), is configured to filter for a frequency above and/or below the nominal frequency, such that a filtered portion of the pixels may have visibility of the frequency shift. In some embodiments, the modulation of the frequency of the monochromatic light enables the pixels of the at least one photodetector array to observe a signal response over a variety of frequencies surrounding a nominal frequency of the monochromatic light. For example, the at least one photodetector array may be configured to detect IR light in a narrow band associated with the nominal frequency. When the emitted frequency is higher than the nominal frequency due to the modulation, the detection of down-shifted light may be more detectable by the at least one photodetector array 260. When the emitted frequency is lower than the nominal frequency due to the modulation, the detected of up-shifted light may be more detectable. Any suitable frequency response technique, including the foregoing, and/or a combination of techniques may be used.

In some embodiments, the at least one aperture 225 operatively connected to the laser emitter 245 may be disposed on a probe unit (not shown) extending at least partially out from the distal end 205 of the medical device 135. Close proximity and/or contact of the emission of the monochromatic light and the target tissue may improve the signal response for generating the Raman spectroscopy image data. In some embodiments, one or more of the at least one photodetector array 260 may be disposed on the probe unit. Close proximity and/or contact of the at least one photodetector array 260 for detecting the scattered monochromatic light may improve signal response for generating the Raman spectroscopy data. In some embodiments, operation of the laser emitter 245 may be triggered, e.g., by the medical provider 115 and/or automatically, in response to proximity and/or contact between the probe unit and the target tissue.

The visible light emitter 250 may be configured to emit visible light, e.g., white light. The visible light emitter 250 may be operatively connected to the at least one aperture 225, e.g., by the at least one fiber optic line 230, such that white light emitted by the visible light emitter 250 is emitted out from the distal end 205 of the medical device 135 via the aperture 225. The visible light may reflect off of the target tissue, e.g., to illuminate the interior of the body of the patient 130.

The at least one photodetector array 260 may be further configured to receive reflected visible light and generate visible image data. For example, the at least one photodetector array 260 may include an RGB-IR photodetector array configured to detect both the monochromatic light of the laser emitter 245 and the visible light of the visible light emitter 250, and to generate both the Raman spectroscopy image data and the visible image data. In an exemplary embodiment, the RGB-IR photodetector array may include a Complementary Metal-Oxide Semiconductor (CMOS) RGB-IR photodetector array. In another exemplary embodiment, the RGB-IR photodetector array may include a multiband CMOS sensor, e.g., with a multi-storied photodiode structure. For example, a top layer of the array may include a pixel array configured to detect visible light. The top layer may be configured to transmit IR light, and a second layer may be configured to detect the transmitted IR light. In a further example, different pixels of the pixel array of the top layer may transmit different wavelengths of IR light, such that the second layer is usable to generate a multiband IR image. It should be understood that the foregoing examples are illustrative only, and that any suitable RGB-IR photodetector array may be used.

The demodulation device 270 may be operatively connected to the at least one photodetector array 260, and may be configured to one or more of demodulate and filter signals and/or data generated by the at least one photodetector array 260. For example, the demodulation device 270 may be configured to demodulate the intermodulation frequency of the modulation device 265 from the Raman spectroscopy image data generated by the at least one photodetector array 260. In another example, the demodulation device 270 may apply one or more of a filter, e.g., a low pass filter, or an amplifier to the Raman spectroscopy image data generated by the at least one photodetector array 260. In some embodiments, the modulation device 265 and the demodulation device 270 operate as or are included with a lock-in circuit, e.g., a lock-in amplifier. A lock-in amplifier may increase a signal strength, fidelity, and/or clarity of the Raman spectroscopy image data.

In some embodiments, the at least one photodetector array 260 may include a plurality of photodetector arrays, e.g., a first photodetector array configured to detect the monochromatic light and a second photodetector array configured to detect the visible light. In some embodiments, a wide-band photodetector array may be used in conjunction with an emitter configured to discretely rotate between different colors and/or frequencies of light, whereby frequency responses for different colors and/or frequencies may be composited together.

In some embodiments, different photodetector arrays may be operatively connected to different apertures 225, e.g., via different fiber optic lines 230. A single multi-frequency array may facilitate analysis and/or tissue characterization, e.g., by facilitating registration between Raman spectroscopy image data and visible image data, as discussed in more detail below. Separate arrays may reduce component cost, or improve a fidelity of generated data.

In some embodiments, the at least one photodetector array 260 may include one or more photodetector arrays configured to detect light of a variety of frequencies. In some embodiments, different optical elements 227 (FIG. 2B), e.g., red, green blue, or IR filters) may be applied to different portions of an aperture 225 or different apertures 225 such that, for example, different portions of the one or more photodetector arrays 260 are configured to detect light of different frequencies, different intensities, different directions of incidence, etc. In exemplary embodiments, a wide-band photodetector array may be combined with a pattern of filters to form an RGB-G visible light photodetector array, and IR photodetector array configured to detect different IR frequencies, an RGB-IR photodetector array, or the like. In some embodiments, the optical element(s) 227 may be applied to the at least one photodetector array 260 instead of or in addition to being applied to the at least one aperture 225.

While the at least one photodetector array 260 in the embodiment depicted in FIG. 2A is positioned in the proximal end 210 and operatively connected to the aperture(s) 225 via fiber optic line(s) 230, in some embodiments, at least one photodetector array, e.g., an IR detector array, a visible light detector array, both, or an RGB-IR detector array, may be instead positioned at the distal end 205 so as to be operatively engaged with the aperture(s) 225. Positioning the at least one photodetector array 260 in the proximal end 210 may facilitate configuring the distal end 205 and/or tube 215 as a disposable component, and may reduce a size of one or more of the distal end 205 or tube 215. A smaller size distal end 205 or tube 215 may reduce an impact on the body of the patient 130, improve a navigability of the medical device 135, or provide room for other components or working channels in the medical device 135. Positioning the at least one photodetector array 260 at the distal end 205 may improve a fidelity of generated data, or may reduce signal noise or the like resulting from the fiber-optic line(s) 230.

In some embodiments, each of the laser emitter 245 and the visible light emitter 250 are operatively connected to a respective aperture 225 via a respective fiber optic line 230. In the embodiment depicted in FIG. 2A, the laser emitter 245 and the visible light emitter 250 are operatively connected to a single fiber optic line 230 via the selectable connector 275. The selectable connector 275 may be operable to selectively alternate a connection of the single fiber optic line 230 between the laser emitter 245 and the visible light emitter 250. In some embodiments, the emitters may be operatively connected to a single fiber optic line 230 via the selectable connector 275. In some embodiments, the medical device 135 may include only a single fiber line 230 and a single aperture 225. In some embodiments, the medical device may include a first fiber optic line for the emitter(s) and a second fiber optic line for the detector array(s).

In some embodiments, one or both of the laser emitter 245 and the visible light emitter 250 may instead be positioned at the distal end and operatively engaged with the aperture(s) 225. Positioning one or both of the emitters at the proximal end 210 may facilitate configuring the distal end 205 and/or tube 215 to be disposable. Positioning one or both of the emitters at the distal end 205 may reduce the need for fiber optic lines. In some embodiments, the emitter(s) and the detector array(s) may all be positioned at the distal end, and the medical device may not require any fiber optic lines.

The controller 255 may be configured to one or more of operate the laser emitter 245, the modulation device 265, the visible light emitter 250, the demodulation device 270, or the selectable connector 275. In some embodiments, the controller 255 may include a memory storing instructions for the operation of the medical device 135. In some embodiments, the controller 255 may be configured to receive instructions from one or more interface 240 of the medical device 135, e.g., a user control, a data connection to another device such as the image processing device 140, the user device 105, or the like.

In some embodiments, the controller 255 may be positioned or at least partially integrated into a device other than the medical device 135. For example, in some embodiments, the controller 255 may be positioned in the image processing device 140, the user device 105, or the like, and may operate the medical device 135 via the interface 240.

Figure 3:
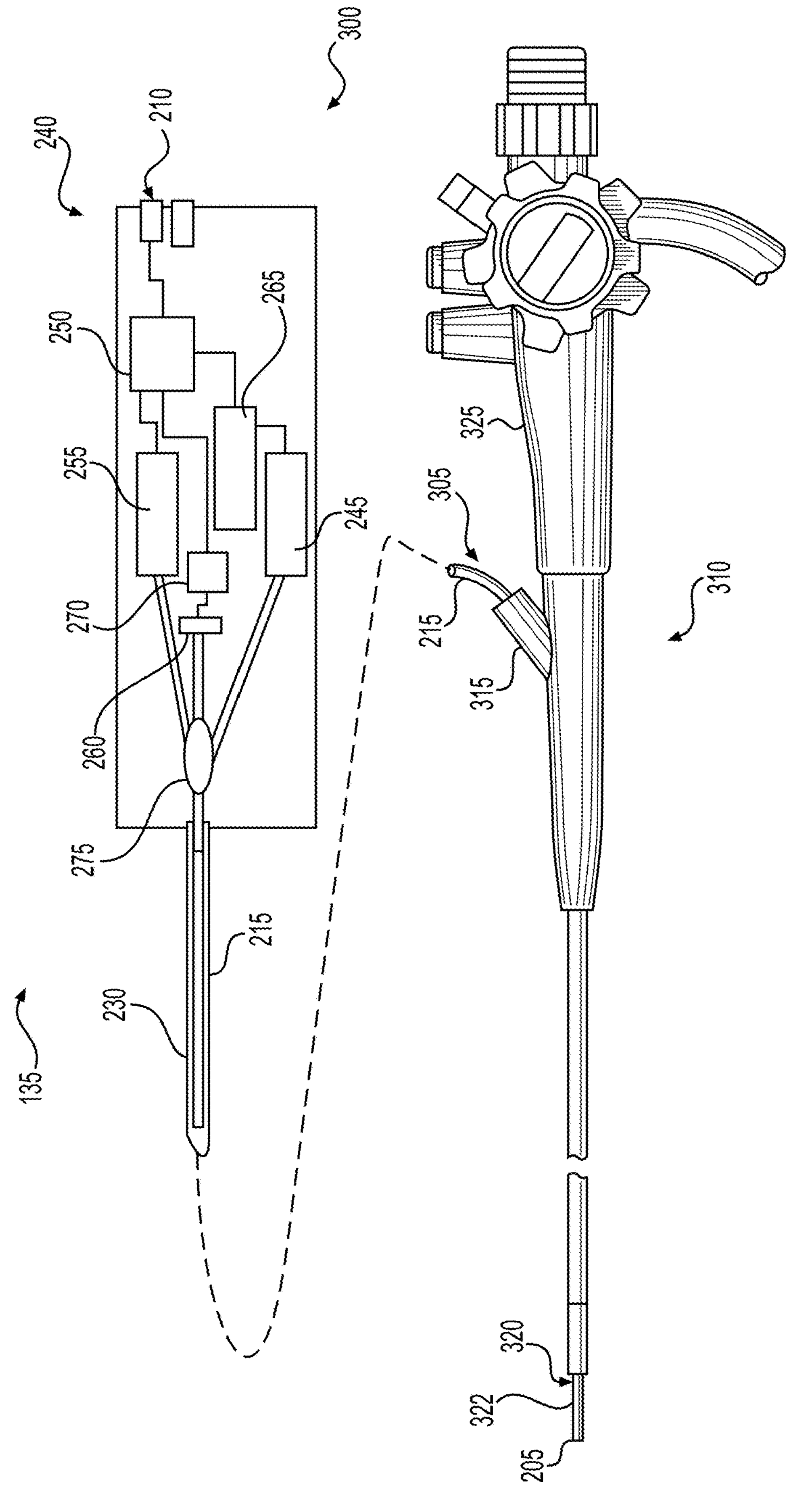
FIG. 3 depicts another exemplary embodiment of the medical device from the system of FIG. 1.

FIG. 3 depicts another exemplary embodiment 300 of the medical device 135. Similar components and devices between the embodiment 200 of FIG. 2A and the embodiment 300 are referred to by similar reference numbers. It should be understood that one or more features of the embodiment 200 may be incorporated into the embodiment 300 in any suitable manner.

In this embodiment 300, the medical device 135 may be configured to operate in conjunction with a working channel 305 of an endoscope device 310. For example, the distal end 205 of the medical device may be advanced into a port at a proximal end 315 of the working channel 305 toward a distal end 320 of the endoscope device 310 such that a portion 322 of the medical device 135 may extend out from the distal end 320 of the endoscope device 310. In some embodiments, the proximal end 210 of the medical device 135 may be configured to engage with a proximal end 325 of the endoscope device 310, e.g., via a clip, strap, or the like (not shown). In some embodiments, the medical device 135 may not include openings for components or working channels of its own. The embodiment 300 or the like may facilitate characterizing tissue of the patient 130 using, for example, a conventional endoscope device and/or a disposable endoscope device as the endoscopic device 310.

Further aspects of the medical device 135 and the image processing device 140 and/or how they may be utilized to characterize target tissue within the body of a patient 130 are discussed in further detail in the methods below. In the following methods, various acts may be described as performed or executed by a component from FIG. 1, such as the medical device 135, the user device 105, the image processing device 140, or components thereof. However, it should be understood that in various embodiments, various components of the system 100 discussed above may execute instructions or perform acts including the acts discussed below. An act performed by a device may be considered to be performed by a processor, actuator, or the like associated with that device. Further, it should be understood that in various embodiments, various steps may be added, omitted, and/or rearranged in any suitable manner.

Figure 4:
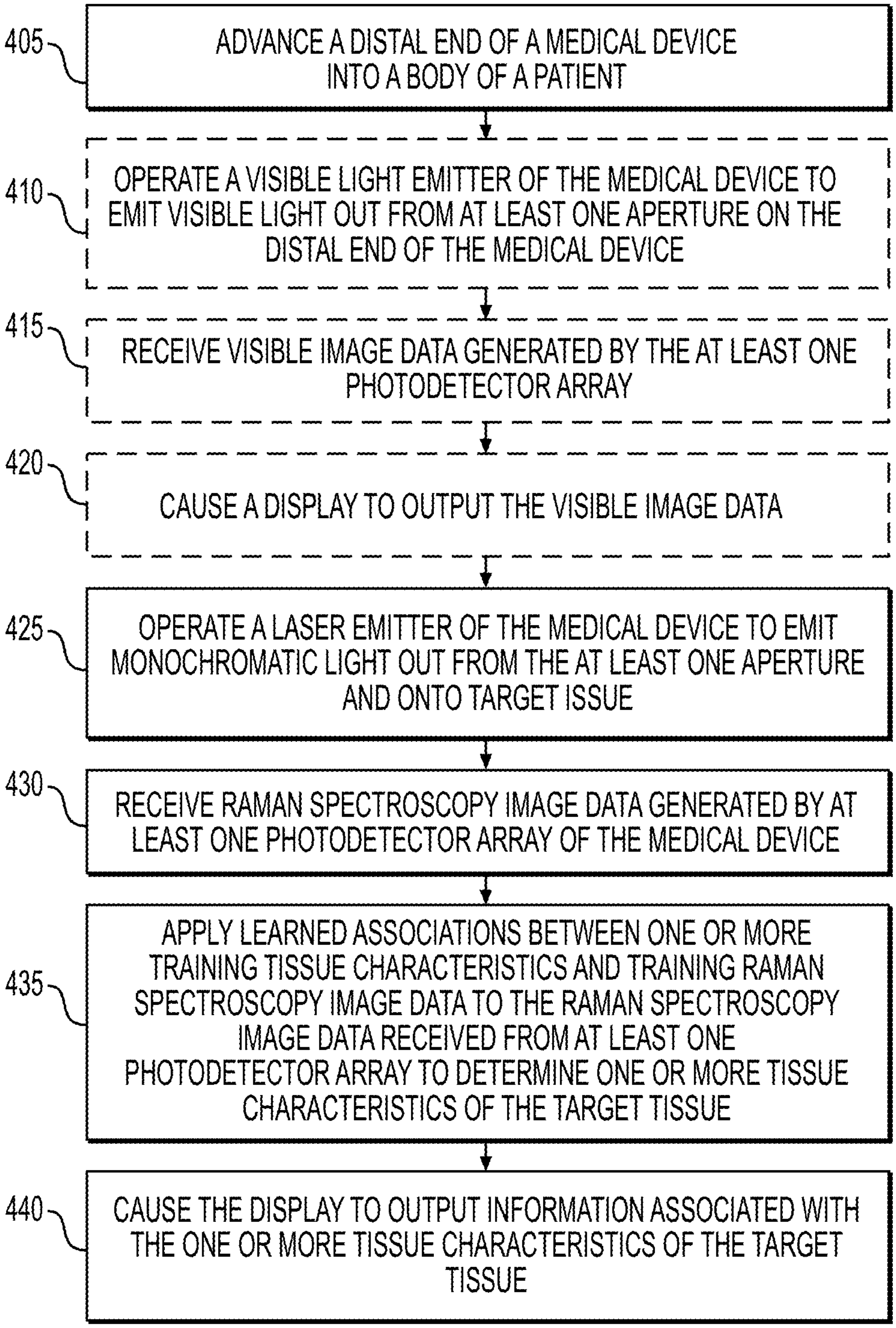
FIG. 4 depicts a flowchart of an exemplary method for determining one or more characteristics of tissue within the body of a patient, according to one or more embodiments.

FIG. 4 illustrates an exemplary process for determining one or more characteristics of tissue within a body of a patient 130. At step 405, a medical provider 115 may advance a distal end 205 of a medical device 135 into the body of the patient 130, e.g., in the course of an endoscopic procedure.

Optionally, at step 410, a controller 255 may operate a visible light emitter 250 of the medical device 135 to emit visible light out from at least one aperture 225 on the distal end 205 of the medical device in order to, for example, illuminate an interior of the body of the patient 130.

Optionally, at step 415, the image processing device 140 may receive visible image data generated by the at least one photodetector array 260, e.g., in response to visible light incident on the at least one aperture 225 that is reflected by the interior of the body of the patient 130.

Optionally, at step 420, the image processing device 140 may cause a display 110 to output the visible image data. In some embodiments, the visible image data may be output in the form of a video, e.g., a live video depicting an endoscopic view of the interior of the body of the patient 130.

At step 425, the controller 255 may operate a laser emitter 245 of the medical device 135 to emit monochromatic light out from the at least one aperture 225 and onto target tissue. In some embodiments, operating the laser emitter 245 includes operating a modulation device 265 configured to modulate a frequency of the monochromatic light emitted by the laser emitter 245.

At step 430, an image processing device 140 may receive Raman spectroscopy image data generated by at least one photodetector array 260 of the medical device 135, e.g., in response to monochromatic light incident on the at least one aperture 225 that is one or more of scattered by or reflected from the target tissue. In some embodiments, each operation of the laser emitter 245 may correspond to a discrete instance of Raman spectroscopy image data. In some embodiments, multiple exposures may be used to generate Raman spectroscopy image data. In other words, the data generated in response to multiple operations of the laser emitter 245 may be composited together to generate an instance of Raman spectroscopy image data. In some embodiments, the Raman spectroscopy image data generated by the at least one photodetector array 260 may be demodulated, filtered, and/or amplified by a demodulation device 270.

In some embodiments, the controller 255 may be configured to alternatingly operate the laser emitter 245 and the visible light emitter 250, e.g., in order to alternatingly acquire Raman spectroscopy image data and visible image data over time. In some embodiments the controller 255 may be configured to alternatingly operate the laser emitter 245 and the visible light emitter 250 such that operation of the laser emitter 245 is interlaced between frames of the live video feed. For example, in some embodiments, the video output via the display 110 may have a frame rate of about 30 frames per second, thus corresponding to a sampling rate of the at least one photodetector array 260 of visible light of 30 samples per second. The controller may thus operate the laser emitter 245 during periods of time between the 30 samples per second used by the at least one photodetector array 260 to detect visible light.

In some embodiments, the laser emitter 245 and the visible light emitter 250 may be operated concurrently. For example, the at least one photodetector array 260 may be able to discretely detect visible light and monochromatic light, such that operation of the laser emitter 245 and the visible light emitter 250 does not prevent detection of visible light and monochromatic light, respectfully, by the at least one photodetector array. In some embodiments, the demodulation device 270 and/or the image processing device 140 or the like may apply one or more filters or analysis processes to data generated by the at least one photodetector array 260 to separate Raman spectroscopy image data and/or visible image data from the generated data.

At step 435, the image processing device 140 may apply learned associations between one or more training tissue characteristics and training Raman spectroscopy image data to the Raman spectroscopy image data received from the at least one photodetector array 260 to determine one or more tissue characteristics of the target tissue. In various embodiments, any suitable application of learned associations may be used such as, for example, a branched-tree algorithm, a comparison of the Raman spectroscopy image data to one or more predetermined criteria, an evaluation of one or more metrics associated with the one or more tissue characteristics, inputting the Raman spectroscopy image data into a trained machine-learning model, or combinations thereof.

In some embodiments, the trained machine-learning model may have been used to develop the learned associations, the predetermined criteria, the metrics, or the like. In some embodiments, the trained machine-learning model may have developed the learned associations based on the one or more training tissue characteristics as ground truth and the training Raman spectroscopy image data as training data. In some embodiments, the trained machine-learning model may be configured to use the learned associations to output the one or more tissue characteristics of the target tissue in response to the input of the Raman spectroscopy image data. As discussed in further detail below, in some embodiments, the trained machine-learning model may be trained based on and/or configured to use as inputs, e.g., for determining the one or more characteristics of the target tissue, additional data such as, for example, visual image data, medical imaging data, patient data, location data, or the like.

At step 440, the image processing device 140 may cause the display 110 to output information associated with the one or more tissue characteristics of the target tissue.

In some embodiments, the image processing device 140 may be configured to output the information associated with the one or more tissue characteristics of the target tissue in conjunction with the output of the visible image data. For example, in some embodiments, the image processing device 140 may register, based on the Raman spectroscopy image data, one or more regions of the visible image data; that correspond with the one or more tissue characteristics of the target tissue. In some embodiments, the registration may be based on a correspondence between pixel locations in the Raman spectroscopy image data and pixel locations in the visible image data. In some embodiments, the registration may be based on features within the Raman spectroscopy image data and pixel locations in the visible image data. In some embodiments, the registration may be based on a correspondence to geometric information describing the interior of the body of the patient 130, e.g., medical imaging data that includes a three-dimensional model, or the like.

In some embodiments, outputting the information associated with the one or more tissue characteristics of the target tissue in conjunction with the output of the visible image data may include generating one or more visual indicators associated with the one or more tissue characteristics of the target tissue, and causing the display 110 to overlay the one or more visual indicators on the live video feed at the one or more corresponding regions.

Figure 5:
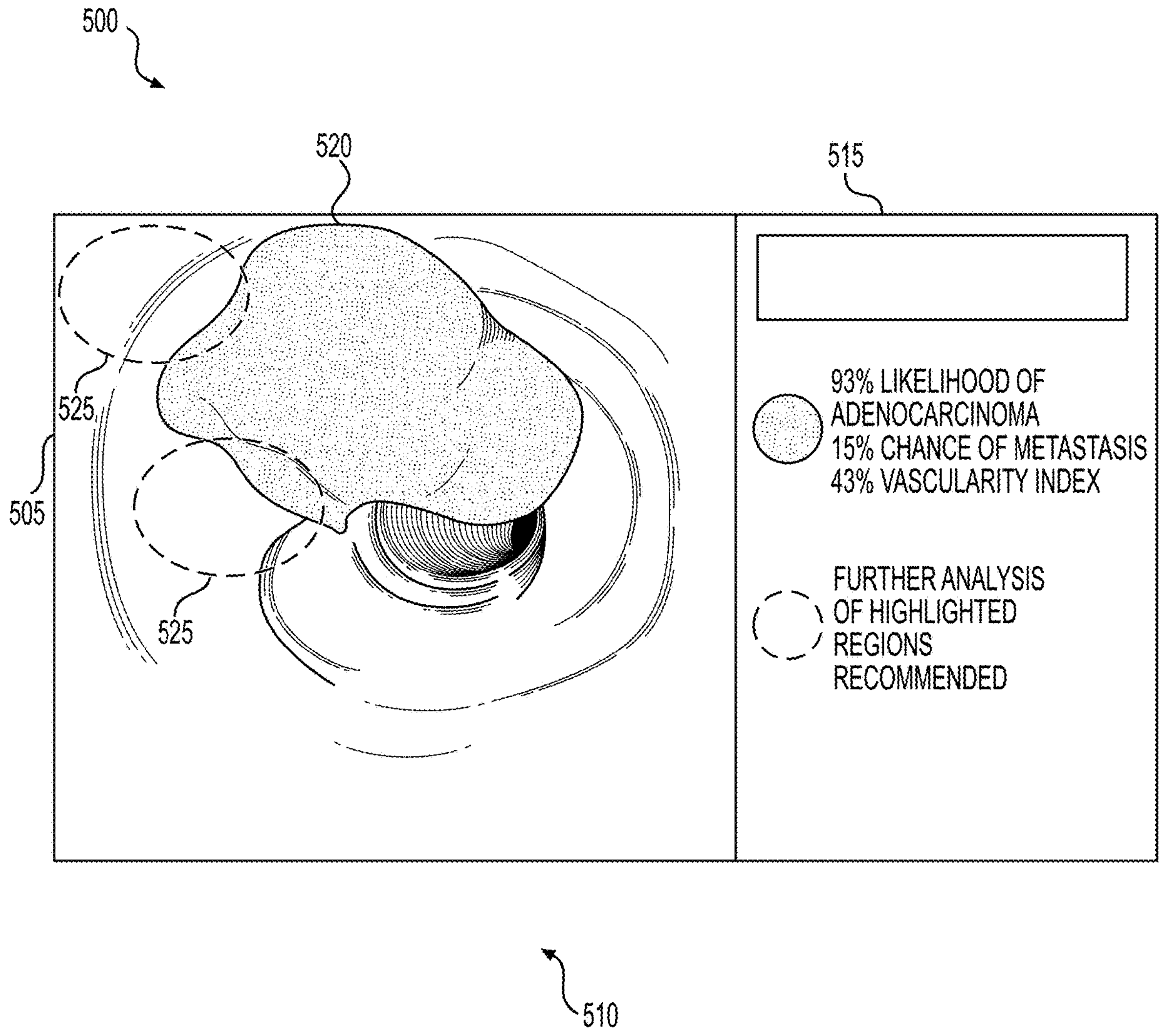
FIG. 5 depicts an exemplary embodiment of an output generated by the system of FIG. 1.

FIG. 5 depicts an exemplary embodiment of an output endoscopic view 500 that may be displayed by the image processing device 140 via the display 110. The endoscopic view 500 includes a live video 505 depicting an interior 510 of the body of a patient 130, an information output 515, and visual indicators 520 and 525.

The live video 505 may be based on visible image data generated from at least one photodetector array 260, such as in one or more of the examples above. The interior 510 of the body of the patient 130 may be, for example, illuminated by a visible light emitter 250, such as in one or more of the examples above. The information output 515 may include information descriptive of the one or more tissue characteristics of tissue in the depicted interior 510 of the body of the patient 130. The visual indicators 520 and 525 may identify locations of the tissue depicted in the interior 510 that correspond to the determined one or more tissue characteristics in the information output 515.

For example, as depicted in FIG. 5, the one or more tissue characteristics in the information output 515 include (i) an identification of a lesion as well as characteristics of the identified lesion including likelihood of malignancy, e.g., of adenocarcinoma, chance of metastasis, and vascularity index, and (ii) an indication that further analysis of one or more region(s) (e.g., via biopsy) is recommended. The visual indicator 520 may have a coloring or other visual identifier that corresponds to the information output (i), and has a shape configured to define a border of a region identified as the lesion. The visual indicators 525 may have a coloring or other visual identifier that corresponds to the information output (ii), and have a shape configured to define a border of regions identified for further analysis.

In an exemplary use case example, the endoscopic view 500 described above may be provided by the display 110 during the normal course of an endoscopic procedure, e.g., while a medical provider 115 navigates the medical device 135 through the body of the patient 130. Thus, in addition to a live video 505 of the interior of the body of the patient 130, the medical provider 115 may be further provided with a live overlay of tissue characterization information. Since the overlay may be provided in real-time or near real-time, the medical provider 115 may determine one or more characteristics of tissue within the body of the patient 130 without having to stop the navigation of the medical device 135 to take a discrete sampling. Further, the information provided by the overlay may one or more of identify regions for further analysis that may not have been identifiable via visual inspection, may facilitate accurate biopsy sampling, and/or may reduce or obviate the need for taking a biopsy.

Figure 6:
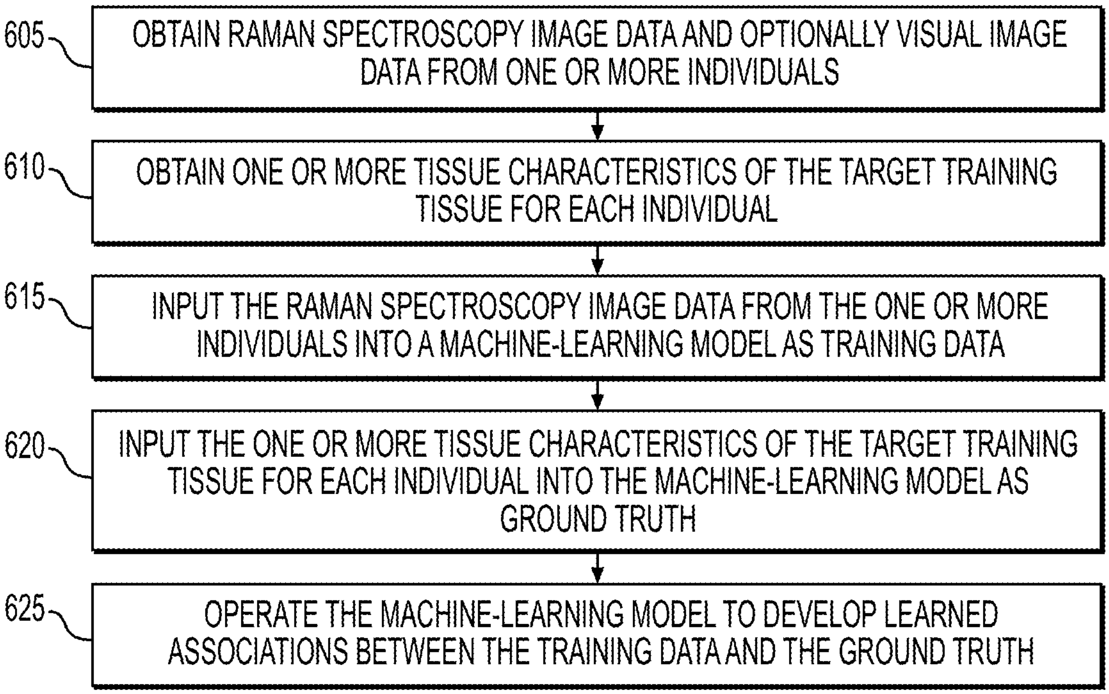
FIG. 6 depicts a flowchart of an exemplary method for training a machine-learning model for determining one or more characteristics of tissue within the body of a patient, according to one or more embodiments.

FIG. 6 illustrates an exemplary process for training a machine-learning model to determine characteristics of tissue within a body of a patient 130, such as in the various examples discussed above. At step 605, a medical provider 115 may obtain Raman spectroscopy image data and optionally visual image data from one or more individuals. Obtaining Raman spectroscopy image data from an individual may include, for example, advancing a medical device 135 into the body of the individual, causing a laser emitter of the medical device 135 to emit monochromatic light out from at least one aperture 225 included on a distal end 205 of the medical device 135 and onto target training tissue of the individual, and receiving Raman spectroscopy image data generated by at least one photodetector array 260 of the medical device 135 that is configured to receive light incident on the at least one aperture 225 that is one or more of scattered by or reflected from the target training tissue of the individual. Any suitable technique for obtaining the visual image data may be used, such as techniques discussed in one or more embodiments above.

At step 610, the medical provider 115 may obtain one or more tissue characteristics of the target training tissue for each individual. The one or more tissue characteristics may be obtained, for example, via biopsy, via visual inspection, from medical records associated with the target training tissue such as pathology data, or via any other suitable technique(s).

At step 615, the medical provider 115 may input the Raman spectroscopy image data and optionally the visible image data from the one or more individuals into a machine-learning model as training data. At step 620, the medical provider 115 may input the one or more tissue characteristics of the target training tissue for each individual into the machine-learning model as ground truth. In some embodiments, the visible image data may be used to cross-correlate the Raman spectroscopy image data with the one or more tissue characteristics. At step 625, the machine learning model may be operated to develop learned associations between the training data and the ground truth.

In some embodiments, additional data from each individual is further input as training data such as, for example, medical imaging data of each individual, patient data of each individual, visible image data of each individual, or the like. In some embodiments, training data for each individual is input as a sequence corresponding to a navigation of the medical device 135 through the body of the individual. In some embodiments, the machine learning model may be at least partially pre-trained prior to the input of the training data and the ground truth.

Figure 7:
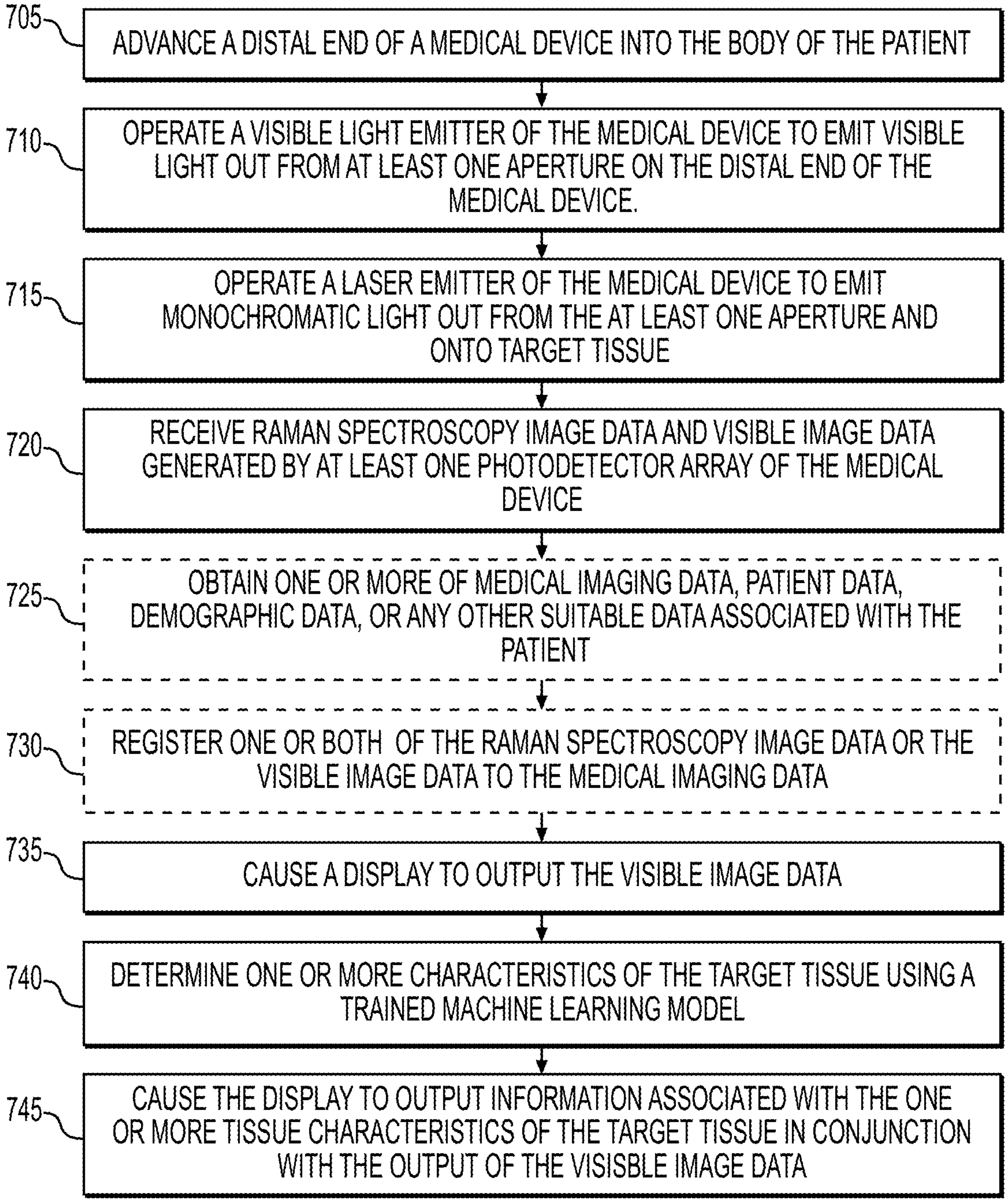
FIG. 7 depicts a flowchart of another exemplary method for determining one or more characteristics of tissue within the body of a patient, according to one or more embodiments.

FIG. 7 illustrates another exemplary process for determining one or more tissue characteristics of tissue within the body of a patient 130, whereby the process utilizes a trained machine-learning model such as a machine-learning model trained according to one or more embodiments discussed above. At step 705, a medical provider 115 may advance a distal end 205 of a medical device 135 into the body of the patient 130, e.g., in the course of an endoscopic procedure.

At step 710, a controller 255 may operate a visible light emitter 250 of the medical device 135 to emit visible light out from at least one aperture 225 on the distal end 205 of the medical device in order to, for example, illuminate an interior of the body of the patient 130. In some embodiments, a video feed may be generated using, for example, at least one photodetector array 260. The video feed may, in some embodiments, be used to select a location for Raman spectroscopy investigation and/or for navigation of the medical device 135 within the body of the patient.

At step 715, the controller 255 may operate a laser emitter 245 of the medical device 135 to emit monochromatic light out from the at least one aperture 225 and onto target tissue. In some embodiments, operating the laser emitter 245 includes operating a modulation device 265 configured to modulate a frequency of the monochromatic light emitted by the laser emitter 245.

At step 720, an image processing device 140 may receive Raman spectroscopy image data and visible image data generated by the at least one photodetector array 260 of the medical device 135, e.g., in response to monochromatic light and visible light, respectively, that is incident on the at least one aperture 225 due to scattering and/or reflection from the target tissue. In some embodiments, the Raman spectroscopy image data generated by the at least one photodetector array 260 may be demodulated, filtered, and/or amplified by a demodulation device 270.

Optionally, at step 725, the image processing device 140 may obtain one or more of medical imaging data, patient data, demographic data, or any other suitable data associated with the patient 130, e.g., from the data storage system 120. In some embodiments, the medical provider 115 may perform medical imaging during or in conjunction with the endoscopic procedure.

Optionally, at step 730, the image processing device 140 may register one or both of the Raman spectroscopy image data or the visible image data to the medical imaging data, e.g., to generate three-dimensional Raman spectroscopy data and/or to generate a three-dimensional reconstruction based on the visible image data.

At step 735, the image processing device 140 may cause a display 110 to output the visible image data. In some embodiments, the visible image data may be output in the form of a video, e.g., a live video depicting the interior of the body of the patient 130.

At step 740, the image processing device 140 may determine one or more characteristics of the target tissue using a trained machine learning model. In various embodiments, using the trained machine-learning model includes inputting Raman spectroscopy data and optionally additional data into the trained machine-learning model. The additional data may include, for example, one or more of the visible image data, the medical imaging data, the patient data, the demographic data, the three-dimensional Raman spectroscopy data, the three-dimensional reconstruction, or the like. The trained machine-learning model may be configured to apply learned associations to the input data that were developed based on training data associated with training target tissue, e.g., of the same type or types as the input data, and training tissue characteristics of the training target tissue.

In some embodiments, multiple trained machine-learning models may be used. For example, a first trained machine-learning model may include a CNN configured to detect features in input image data, and a second trained machine-learning model may be configured to determine one or more tissue characteristics in target tissue based on an input of the detected features output form the first trained machine-learning model. Any suitable number and arrangement of machine-learning models may be used.

At step 745, the image processing device 140 may cause the display 110 to output information associated with the one or more tissue characteristics of the target tissue in conjunction with the output of the visible image data, such as in one or more of the examples discussed above.

It should be understood that embodiments in this disclosure are exemplary only, and that other embodiments may include various combinations of features from other embodiments, as well as additional or fewer features. For example, while some of the embodiments above pertain to identifying biopsy locations and/or replacing a biopsy with an in-situ tissue characterization, any suitable activity may be used. In an exemplary embodiment, instead of or in addition to activities that conventionally include biopsies, the techniques according to this disclosure may be similarly adapted to polyp screening and/or removal during a colonoscopy, endoscopic submucosal dissection, etc. In some embodiments, data resulting from a procedure, such as those described in one or more of the examples above, may be stored in the data storage system 120, e.g., to be used for further training of the machine-learning model, such as when additional information regarding the target tissue has been determined via a biopsy or the like. In some embodiments, such data may be fed into an endoscopic report generating application and/or an electronic medical records system.

In another example, while some of the embodiments above pertain to the use of a photodetector array, e.g., a photodiode array, to generate Raman spectroscopy image data, it should be understood that any suitable sensor for generating Raman spectroscopy image data may be used.

In some embodiments, the image processing device 140, or the like, may be configured to generate a notification in response to a trigger condition such as detection of abnormal tissue. Another trigger condition may include, for example, a particular characterization of tissue, a confidence level for a tissue characterization, a size of tissue having a particular characterization, a location of the tissue having the particular characterization, or the like. The notification may include, for example, a further visual indicator, an audible alert, an electronic message, or may be included in data and/or a report associated with the endoscopic procedure.

In general, any process or operation discussed in this disclosure that is understood to be computer-implementable, such as the processes illustrated in FIGS. 4, 6, and 7, may be performed by one or more processors of a computer system, such any of the components or devices in the system 100 of FIG. 1, as described above. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples above, may include one or more computing devices, such as one or more of the systems or devices in FIG. 1. One or more processors of a computer system may be included in a single computing device or distributed among a plurality of computing devices. A memory of the computer system may include the respective memory of each computing device of the plurality of computing devices.

Figure 8:
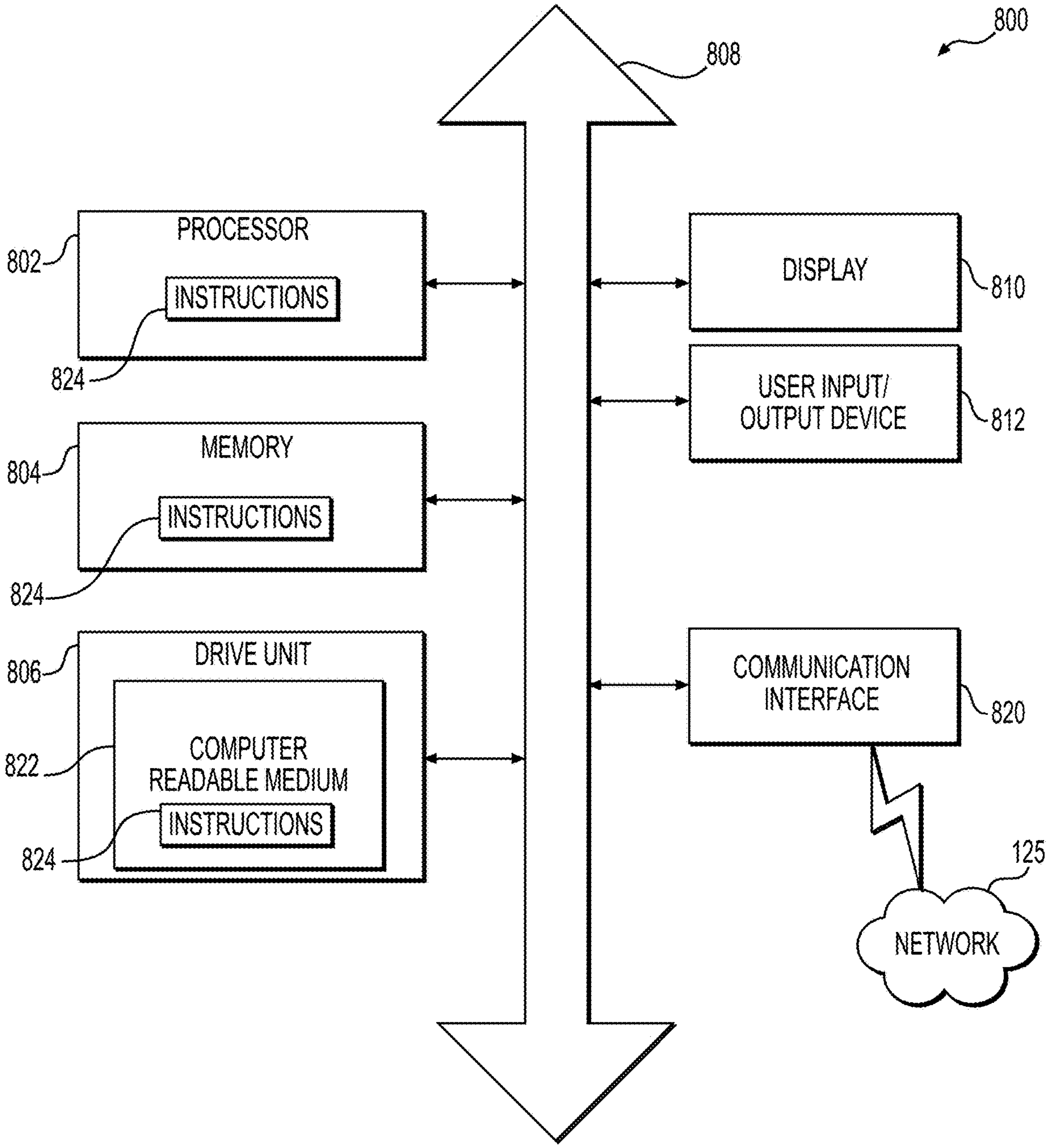
FIG. 8 depicts an example of a computing device, according to one or more embodiments.

FIG. 8 is a simplified functional block diagram of a computer 800 that may be configured as a device for executing the methods of FIGS. 2 and 3, according to exemplary embodiments of this disclosure. For example, the computer 800 may be configured as the controller 255 of the medical device 135, the user device 105, the image processing device 140, and/or another system according to exemplary embodiments of this disclosure. In various embodiments, any of the systems or devices herein may be a computer 800 including, for example, a data communication interface 820 for packet data communication. The computer 800 also may include a central processing unit ("CPU") 802, in the form of one or more processors, for executing program instructions. The computer 800 may include an internal communication bus 808, and a storage unit 806 (such as ROM, HDD, SDD, etc.) that may store data on a computer readable medium 822, although the computer 800 may receive programming and data via network communications. The computer 800 may also have a memory 804 (such as RAM) storing instructions 824 for executing techniques presented herein, although the instructions 824 may be stored temporarily or permanently within other modules of computer 800 (e.g., processor 802 and/or computer readable medium 822). The computer 800 also may include input and output ports 812 and/or a display 810 to connect with input and output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible “storage” media, terms such as computer or machine “readable medium” refer to any medium that participates in providing instructions to a processor for execution.

While the disclosed methods, devices, and systems are described with exemplary reference to transmitting data, it should be appreciated that the disclosed embodiments may be applicable to any environment, such as a desktop or laptop computer, an automobile entertainment system, a home entertainment system, etc. Also, the disclosed embodiments may be applicable to any type of Internet protocol.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of this invention.

The above disclosed subject matter is to be considered illustrative, and not restrictive, and the appended claims are intended to cover all such modifications, enhancements, and other implementations, which fall within the true spirit and scope of this disclosure. Thus, to the maximum extent allowed by law, the scope of this disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

What is claimed is:

1. A computer-implemented method for image data processing to characterize tissue, comprising:

receiving, from a medical device, visible image data of the tissue, and Raman spectroscopy image data of the tissue;

providing the Raman spectroscopy image data as input to a trained machine-learning model, wherein, based on the Raman spectroscopy image data, the trained machine-learning model is configured to identify one or more tissue characteristics of the tissue associated with one or more first regions of the Raman spectroscopy image data;

receiving the one or more tissue characteristics of the tissue as output of the trained machine-learning model;

registering the Raman spectroscopy image data to the visible image data to identify, based on the registering, one or more second regions of the visible image data corresponding to the one or more first regions of the Raman spectroscopy image data that the one or more tissue characteristics of the tissue are associated with;

generating an overlay, the overlay including one or more visual indicators associated with the one or more tissue characteristics at locations in the overlay corresponding to the one or more second regions of the visible image data; and causing a display of the overlay on the visible image data.

2. The computer-implemented method of claim 1, wherein the registering is based on a correspondence between pixel locations in the Raman spectroscopy image data and pixel locations in the visible image data.

3. The computer-implemented method of claim 1, wherein the registering is based on features within the Raman spectroscopy image data and pixel locations in the visible image data.

4. The computer-implemented method of claim 1, wherein generating the overlay includes:

generating the one or more visual indicators to have a shape configured to define a border of the one or more second regions of the visible image data.

5. The computer-implemented method of claim 1, further comprising:

generating an information output based on the one or more tissue characteristics, including one or more of descriptive information of the one or more tissue characteristics or a recommendation based on the one or more tissue characteristics; and causing a display of the information output in conjunction with the overlay on the visible image data.

6. The computer-implemented method of claim 5, wherein each of the one or more visual indicators includes an identifier that corresponds to one or more of the descriptive information or the recommendation included in the information output.

7. The computer-implemented method of claim 1, further comprising:

providing additional data as input to the trained machine-learning model, wherein the one or more tissue characteristics of the tissue are identified further based on the additional data, and wherein the additional data includes one or more of the visible image data, medical imaging data, patient data, location data, three-dimensional Raman spectroscopy image data, or a three-dimensional visible image data reconstruction.

8. The computer-implemented method of claim 1, further comprising:

receiving a three-dimensional model of at least a portion of an interior of a patient’s body including the tissue.

9. The computer-implemented method of claim 8, wherein the registering further comprises:

registering the visible image data and Raman spectroscopy image data to the three-dimensional model.

10. The computer-implemented method of claim 8, further comprising:

generating three-dimensional Raman spectroscopy image data based on the Raman spectroscopy image data and the three-dimensional model, wherein the Raman spectroscopy image data provided as input to the trained machine-learning model is the three-dimensional Raman spectroscopy image data.

11. The computer-implemented method of claim 8, further comprising:

generating a three-dimensional reconstruction of the visible image data based on the visible image data and the three-dimensional model, wherein the three-dimensional reconstruction of the visible image data is provided as further input to the trained machine-learning model.

12. The computer-implemented method of claim 8, further comprising:

receiving a position signal from a location sensor positioned at a distal end of the medical device; and based on the position signal, registering a position of the distal end of the medical device with a location within the three-dimensional model to obtain location data, wherein the location data is provided as further input to the trained machine-learning model.

13. The computer-implemented method of claim 1, wherein the medical device includes a visible light emitter configured to facilitate capture of the visible image data by the medical device, and a laser emitter configured to facilitate capture of the Raman spectroscopy image data by the medical device, and the method further comprises:

causing the medical device to alternatingly operate the visible light emitter and the laser emitter to receive the visible image data and the Raman spectroscopy image data.

14. The computer-implemented method of claim 1, further comprising:

receiving a signal from a location sensor positioned at a distal end of the medical device; and determining location data of the distal end of the medical device based on the signal, wherein the location data is provided as further input to the trained machine-learning model to identify the one or more tissue characteristics.

15. A computing system for processing image data to characterize tissue, the computing system comprising:

at least one memory storing instructions; and at least one processor coupled to the at least one memory and configured to execute the instructions to perform one or more operations including:

receiving, from a medical device removably coupled to the computing system, visible image data of the tissue, and Raman spectroscopy image data of the tissue;

processing, using a trained machine-learning model, the Raman spectroscopy image data to identify a tissue characteristic of a portion of the tissue associated with a first pixel region of the Raman spectroscopy image data;

registering the visible image data to the Raman spectroscopy image data;

identifying a second pixel region of the visible image data corresponding to the first pixel region of the Raman spectroscopy image data based on the registering;

generating an output view including a visual indicator overlaid on the second pixel region of the visible image data, wherein the visual indicator visually indicates the portion of the tissue exhibiting the tissue characteristic; and providing, to a display device removably coupled to the computing system, the output view for display.

16. The computing system of claim 15, wherein generating the output view includes:

generating the visual indicator to have a shape configured to define a border of the second pixel region of the visible image data.

17. The computing system of claim 15, wherein generating the output view further includes:

generating information based on the tissue characteristic, the information including one or more of descriptive information of the tissue characteristic or a recommendation based on the tissue characteristic; and including the information in the output view, wherein the visual indicator includes an identifier that corresponds to one or more of the descriptive information or the recommendation included in the information.

18. The computing system of claim 15, wherein the medical device includes a visible light emitter configured to facilitate capture of the visible image data by the medical device, and a laser emitter configured to facilitate capture of the Raman spectroscopy image data by the medical device, and the one or more operations further include:

causing the medical device to alternatingly operate the visible light emitter and the laser emitter to receive the visible image data and the Raman spectroscopy image data.

19. An imaging system for processing image data to characterize tissue, the imaging system comprising:

a medical device including a visible light emitter and a laser emitter configured to respectively facilitate capture, by the medical device, of visible image data of the tissue, and Raman spectroscopy image data of the tissue; and a computing system to which the medical device is removably coupled to, the computing system comprising:

at least one memory storing instructions; and at least one processor coupled to the at least one memory and configured to execute the instructions to perform one or more operations including:

causing the medical device to alternatingly operate the visible light emitter and the laser emitter;

receiving, from the medical device, the visible image data of the tissue as the medical device is operating the visible light emitter;

causing the visible image data to be displayed on a display device removably coupled to the computing system;

receiving, from the medical device, the Raman spectroscopy image data of the tissue as the medical device is operating the laser emitter;

applying a trained machine-learning model to the Raman spectroscopy image data to identify a tissue characteristic of a portion of the tissue included in a first image region of the Raman spectroscopy image data;

registering the Raman spectroscopy image data and the visible image data with one another to identify a second image region of the visible image data corresponding to the first image region of the Raman spectroscopy image data;

generating a visual indicator to represent a location of the portion of the tissue; and causing an overlay of the visual indicator on the second image region of the visible image data displayed on the display device.

20. The imaging system of claim 19, further comprising:

generating information based on the tissue characteristic, including one or more of descriptive information of the tissue characteristic or a recommendation based on the tissue characteristic; and causing the information to be displayed on the display device in conjunction with the visual indicator overlaid on the visible image data, wherein the visual indicator includes an identifier that corresponds to one or more of the descriptive information or the recommendation included in the information.

* * * * *